(12) United States Patent
Ubbesen et al.

(10) Patent No.: US 11,583,164 B2
(45) Date of Patent: Feb. 21, 2023

(54) VIDEO PROCESSING APPARATUS

(71) Applicant: AMBU A/S, Ballerup (DK)

(72) Inventors: Line Sandahl Ubbesen, Holte (DK); Chin-Tuan Wei, New Taipei (TW)

(73) Assignee: AMBU A/S, Ballerup (DK)

( * ) Notice: Subject to any disclaimer, the term of this patent is extended or adjusted under 35 U.S.C. 154(b) by 50 days.

(21) Appl. No.: 17/327,085

(22) Filed: May 21, 2021

(65) Prior Publication Data

US 2022/0354342 A1    Nov. 10, 2022

(30) Foreign Application Priority Data

May 5, 2021  (DK) .......................... PA 2021 70209

(51) Int. Cl.
*A61B 1/00* (2006.01)
(52) U.S. Cl.
CPC ...... *A61B 1/00048* (2013.01); *A61B 1/00009* (2013.01); *A61B 1/00018* (2013.01); *A61B 1/00114* (2013.01)
(58) Field of Classification Search
None
See application file for complete search history.

(56) References Cited

U.S. PATENT DOCUMENTS

| 4,455,008 A | 6/1984 | Mackew |
| 4,591,120 A * | 5/1986 | Bryant-Jeffries ...... F16M 11/14 248/921 |
| 5,611,513 A | 3/1997 | Rosen |
| 8,526,176 B2 | 9/2013 | Clark et al. |
| 9,220,400 B2 | 12/2015 | Petersen et al. |
| D769,235 S | 10/2016 | Li |

(Continued)

FOREIGN PATENT DOCUMENTS

| CN | 204515643 U | 7/2015 |
| CN | 208837898 | 5/2019 |

(Continued)

OTHER PUBLICATIONS

First Technical Examination issued in Danish Patent Application No. PA 2021 70209, dated Oct. 29, 2021, 9 pages.

(Continued)

*Primary Examiner* — John P Leubecker
*Assistant Examiner* — Minqiao Huang
(74) *Attorney, Agent, or Firm* — Faegre Drinker Biddle & Reath LLP

(57) ABSTRACT

A video processing system including a video processing apparatus (VPA) including: a housing having a top wall with a top wall periphery, a top surface extending to the top wall periphery, and a central area; an input port adapted to receive video input signals from a videoscope; an output connector adapted to transmit video output signals; and a bracket interface supported by the housing and adapted to support a support bracket including a first retention feature, bracket interface located within the central area of the top wall and comprising a bracket base receptacle and a second retention feature, the bracket base receptacle sized and shaped to receive a base end of the support bracket, and the second retention feature sized and shaped to cooperate with the first retention feature to removably retain the base end of the support bracket.

20 Claims, 18 Drawing Sheets

(56) References Cited

U.S. PATENT DOCUMENTS

| | | | |
|---|---|---|---|
| 9,847,002 B2 | 12/2017 | Kiani et al. | |
| 9,880,586 B2 | 1/2018 | Ent | |
| 10,321,804 B2 | 6/2019 | Jacobsen et al. | |
| 10,343,778 B2* | 7/2019 | Peuziat | F16M 11/14 |
| D872,727 S | 1/2020 | Chung | |
| D879,090 S | 3/2020 | Chung | |
| D881,201 S | 4/2020 | Lou | |
| 10,835,106 B1 | 11/2020 | Ubbesen et al. | |
| D917,498 S | 4/2021 | Chiu et al. | |
| 2006/0283903 A1* | 12/2006 | Vitito | B60R 11/0235 |
| | | | 224/400 |
| 2007/0030632 A1* | 2/2007 | Cheng | F16M 11/08 |
| | | | 361/679.06 |
| 2008/0117574 A1* | 5/2008 | Lee | G06F 1/1601 |
| | | | 361/679.06 |
| 2008/0228036 A1* | 9/2008 | Suzuki | G02B 23/2476 |
| | | | 600/136 |
| 2009/0076368 A1* | 3/2009 | Balas | A61B 1/042 |
| | | | 600/407 |
| 2010/0172073 A1* | 7/2010 | Shen | H04N 5/64 |
| | | | 361/679.01 |
| 2011/0069445 A1 | 3/2011 | Haren et al. | |
| 2012/0006767 A1* | 1/2012 | Bennett | F16M 11/12 |
| | | | 211/26 |
| 2012/0155004 A1* | 6/2012 | Yukawa | G06F 1/187 |
| | | | 361/679.21 |
| 2013/0183633 A1* | 7/2013 | Dillon | A61B 1/00048 |
| | | | 433/29 |
| 2015/0196192 A1* | 7/2015 | Kan | F16M 11/42 |
| | | | 211/85.13 |
| 2016/0015362 A1* | 1/2016 | Jones | A61B 8/445 |
| | | | 600/466 |
| 2016/0081539 A1* | 3/2016 | Pagan | A61B 1/00027 |
| | | | 600/184 |
| 2016/0353611 A1 | 12/2016 | Chi et al. | |
| 2017/0127057 A1* | 5/2017 | Sung | H04N 5/225 |
| 2018/0303317 A1 | 10/2018 | Matthison-Hansen | |
| 2019/0053700 A1* | 2/2019 | Tesar | G02B 27/022 |
| 2019/0133430 A1* | 5/2019 | Inglis | A61B 1/00016 |
| 2019/0223694 A1 | 7/2019 | Lund et al. | |
| 2019/0298321 A1* | 10/2019 | Intintoli | A61B 1/00094 |
| 2020/0110956 A1* | 4/2020 | Fan | G06T 7/73 |
| 2021/0173442 A1* | 6/2021 | Luhar | F16B 2/22 |

FOREIGN PATENT DOCUMENTS

| | | |
|---|---|---|
| CN | 209821741 U | 12/2019 |
| JP | 2005-316867 | 11/2005 |
| KR | 1020040102794 | 12/2006 |
| KR | 200442623 Y1 | 11/2008 |

OTHER PUBLICATIONS

GlideScope Core Brochure, Verathon Inc., Jan. 16, 2020, 6 pages.
WildDesign article, Invendoscope E200, circa 2017, 4 pages.
Chameness, Christopher, Veterian Key, Endoscopy, Chapter 27, Jul. 10, 2016, 17 pages.
Written Opinion and International Search Report in International Application No. PCT/EP2022/061686, dated Sep. 8, 2022, 10 pgs.

* cited by examiner

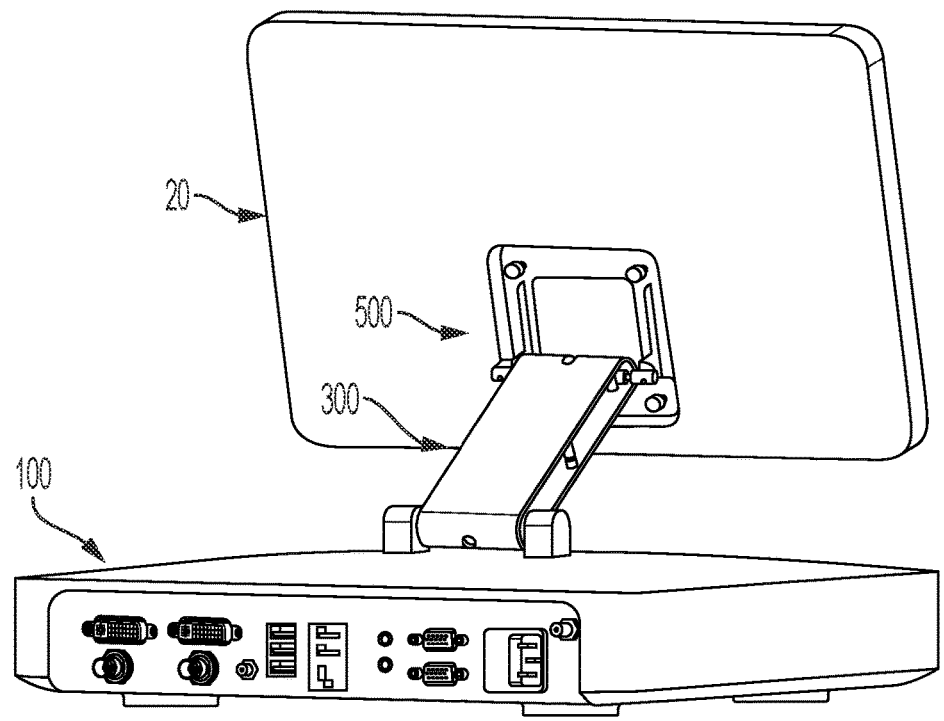
FIG. 26
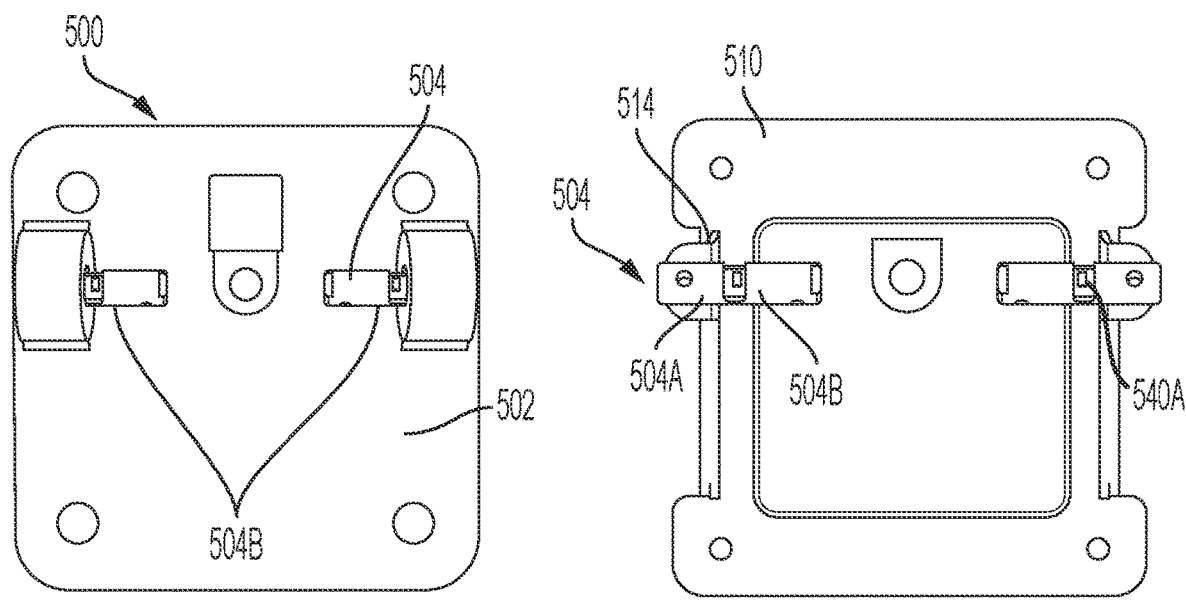
FIG. 27
FIG. 28

VIDEO PROCESSING APPARATUS

CROSS-REFERENCE TO RELATED APPLICATIONS

This application claims priority from and the benefit of Danish Patent Application No. PA 2021 70209, filed May 5, 2021, which is incorporated herein by reference in its entirety.

TECHNICAL FIELD

The disclosure relates to a video processing apparatus operable to output images obtained with a videoscope. More particularly, the disclosure relates to a portable video processing apparatus operable to receive image data from one or more videoscopes and output a video stream corresponding to the image data for presentation with a display module operably coupled to the video processing apparatus.

BACKGROUND OF THE DISCLOSURE

Medical videoscopes comprise endoscopes, colonoscopes, ear-nose-throat scopes, duodenoscopes, and any other medical device having an image sensor configured to obtain images of views of a patient. The term "patient" herein includes humans and animals. Portable medical monitors can be communicatively coupled to the medical videoscopes to receive image data therefrom and present images corresponding to the image data on a display module of the monitor. Traditional medical monitors comprise video processing circuits and a display module combined in a common housing. Such monitors offer many advantages and conveniences in many settings including in the field, emergency response vehicles and hospitals.

Videoscopes are made for various procedures and may have different technical characteristics suited for the procedure they are designed to perform, based on the age of the device, or for other reasons. The technical characteristics, or technology, may comprise the type of image sensor included with the videoscope, whether the videoscope includes on-board data processing capabilities, and whether the videoscope includes additional sensors which provide information to the monitor, potentially including more than one image sensor. The type of image sensor may provide different capabilities, including various controls such as image inversion, image rotation, contrast, and exposure. Thusly, a medical monitor capable of adaptation to different videoscope technologies provides significant value. Examples of such medical monitors are described in commonly owned U.S. Pat. Nos. 10,835,106 and 10,980,397.

An endoscope is a type of a videoscope. An endoscope described in commonly owned U.S. Patent Application No. 2019/0223694 has an insertion tube with an internal working channel and a connector at the handle adapted for the attachment of a syringe. A recess is adapted to accommodate a cylindrical body of the syringe when the syringe is attached to the connector. The endoscope is adapted to perform bronchoalveolar lavage, a procedure for obtaining samples, through the working channel, of organic material from a lung segment of a patient. Commonly owned U.S. Pat. No. 10,321,804 describes an articulated tip of an endoscope. Commonly owned U.S. Pat. No. 9,220,400 describes a camera housing arranged at the distal end of the insertion tube. The camera housing is molded and contains an image sensor and a light source, e.g. LED, embedded in the material of the camera housing. The foregoing application and patents describe technical characteristics of respective videoscopes described therein and are incorporated herein by reference in their entirety.

Furthermore, portable medical monitors with display modules integrated with the medical monitors, as described in commonly owned U.S. Pat. Nos. 10,835,106 and 10,980,397, may have video outputs to present the image data, or video stream, on the communicatively coupled display modules in addition to the presentation with the integrated display module. Upgrading the display module integrated with the medical monitor might not be technically or economically feasible.

Based on the foregoing it is evident that a need exists for an economical apparatus operable with a variety of videoscopes and videoscope technologies in a variety of settings that can also be provided with various display modules.

SUMMARY OF THE DISCLOSURE

The present disclosure relates to a video processing system including a video processing apparatus and a bracket operable to support a display module.

The present disclosure provides solutions which at least improve the solutions of the prior art. The present disclosure provides a video processing apparatus (VPA) for use in a medical environment in which fluids may fall on the VPA. The present disclosure provides a VPA that can be connected to different display modules and can support the display modules in a variety of positions.

In a first aspect of the disclosure, a video processing system comprises a video processing apparatus (VPA) including: a housing having a top wall spaced apart from a bottom wall, the top wall having a top wall periphery, a top surface extending to the top wall periphery, and a central area within the top wall periphery; an input port adapted to receive video input signals from a videoscope; an output connector adapted to transmit video output signals corresponding to the video input signals for presentation with a display module; and a bracket interface supported by the housing and adapted to support a support bracket including a first retention feature, the bracket interface located within the central area of the top wall and comprising a bracket base receptacle and a second retention feature, the bracket base receptacle sized and shaped to receive a base end of the support bracket, and the second retention feature sized and shaped to cooperate with the first retention feature to removably retain the base end of the support bracket.

In some embodiments, the bracket interface defines a bracket interface periphery in the top surface, and the bracket interface periphery is elevated relative to the top wall periphery.

In some embodiments, the top surface extends convexly between the bracket interface periphery and the top wall periphery.

In some embodiments, the top surface extends in a continuous manner from the bracket interface periphery to the top wall periphery.

In some embodiments, the top surface extends in a continuous manner from the bracket interface periphery to the top wall periphery.

In some embodiments, the system comprises the support bracket, including an arm, wherein the base end includes a swivel assembly operable to rotate the arm in a first dimension. The first dimension may be about a first axis of the swivel assembly.

In some embodiments, the support bracket comprises the base end opposite a display end, wherein the arm extends between the base end and the display end, wherein the display end includes a first pivot assembly adapted to rotate a display module in a second dimension different than the first dimension. The second dimension may be about a second axis. The second axis may be perpendicular to the first axis.

In some embodiments, the base end includes a second pivot assembly operable to rotate the arm in the second dimension. The second dimension may be about a third axis parallel to the second axis.

In some embodiments, the swivel assembly comprises a swivel frame, a friction plate, and a pivot assembly support, the friction plate positioned between the swivel frame and the pivot assembly support.

In some embodiments, the friction plate comprises a textured surface configured to provide a predetermined amount of swivel resistance to the swivel assembly.

In some embodiments, the assembly comprises a display module connected to the support bracket by the first pivot assembly.

The foregoing embodiments of the first aspect may be combined and some may be excluded from various systems. For example, the bracket may comprise a standard attachment feature instead of the first pivot assembly to support a display module with a mating standard attachment feature.

In another example, the bracket excludes the first and second pivot assemblies and comprises fixed angles instead.

A system may comprise a set of brackets having different features and the user may thus select a bracket from the set of brackets.

In a second aspect of the disclosure, a video processing system comprises a video processing apparatus (VPA) including: a housing having a top wall spaced apart from a bottom wall, the top wall having a top wall periphery, a top surface extending to the top wall periphery, and a central area within the top wall periphery; an input port adapted to receive video input signals from a videoscope; an output connector adapted to transmit video output signals corresponding to the video input signals for presentation with a display module. The top surface curves between the central area of the top wall and the top wall periphery.

In some embodiments, the top surface extends convexly between the bracket interface periphery and the top wall periphery.

In some embodiments, the top surface extends in a continuous manner from the bracket interface periphery to the top wall periphery.

In some embodiments, the top surface extends in a continuous manner from the bracket interface periphery to the top wall periphery.

In some embodiments, a bracket interface is supported by the housing and adapted to support a support bracket including a first retention feature, the bracket interface located within the central area of the top wall and comprising a bracket base receptacle and a second retention feature, the bracket base receptacle sized and shaped to receive a base end of the support bracket, and the second retention feature sized and shaped to cooperate with the first retention feature to removably retain the base end of the support bracket.

In some embodiments, the bracket interface defines a bracket interface periphery in the top surface, and the bracket interface periphery is elevated relative to the top wall periphery.

In some embodiments, the system comprises the support bracket, including an arm, wherein the base end includes a swivel assembly operable to rotate the arm in a first dimension. The first dimension may be about a first axis of the swivel assembly.

In some embodiments, the support bracket comprises the base end opposite a display end, wherein the arm extends between the base end and the display end, wherein the display end includes a first pivot assembly adapted to rotate a display module in a second dimension different than the first dimension. The second dimension may be about a second axis. The second axis may be perpendicular to the first axis.

In some embodiments, the base end includes a second pivot assembly operable to rotate the arm in the second dimension. The second dimension may be about a third axis parallel to the second axis.

In some embodiments, the swivel assembly comprises a swivel frame, a friction plate, and a pivot assembly support, the friction plate positioned between the swivel frame and the pivot assembly support.

In some embodiments, the friction plate comprises a textured surface configured to provide a predetermined amount of swivel resistance to the swivel assembly.

In some embodiments, the seem comprises a display module connected to the support bracket by the first pivot assembly.

The foregoing embodiments of the second aspect may be combined and some may be excluded from various systems. For example, the bracket may comprise a standard attachment feature instead of the first pivot assembly to support a display module with a mating standard attachment feature.

In another example, the bracket excludes the first and second pivot assemblies and comprises fixed angles instead.

A system may comprise a set of brackets having different features and the user may thus select a bracket from the set of brackets.

BRIEF DESCRIPTION OF THE DRAWINGS

The above-mentioned embodiments and additional variations, features and advantages thereof will be further elucidated by the following illustrative and nonlimiting detailed description of embodiments disclosed herein with reference to the appended drawings, wherein:

FIG. 26 is a perspective view of the embodiment of the video processing system of FIG. 2 showing another pivot assembly of the embodiment of the video processing system of FIG. 2; and FIGS. 27 to 33 are plan and perspective views of components of the pivot assembly of FIG. 26.

In the drawings, corresponding reference characters indicate corresponding parts, functions, and features throughout the several views. The drawings are not necessarily to scale and certain features may be exaggerated in order to better illustrate and explain the disclosed embodiments.

DETAILED DESCRIPTION

Figure 1:
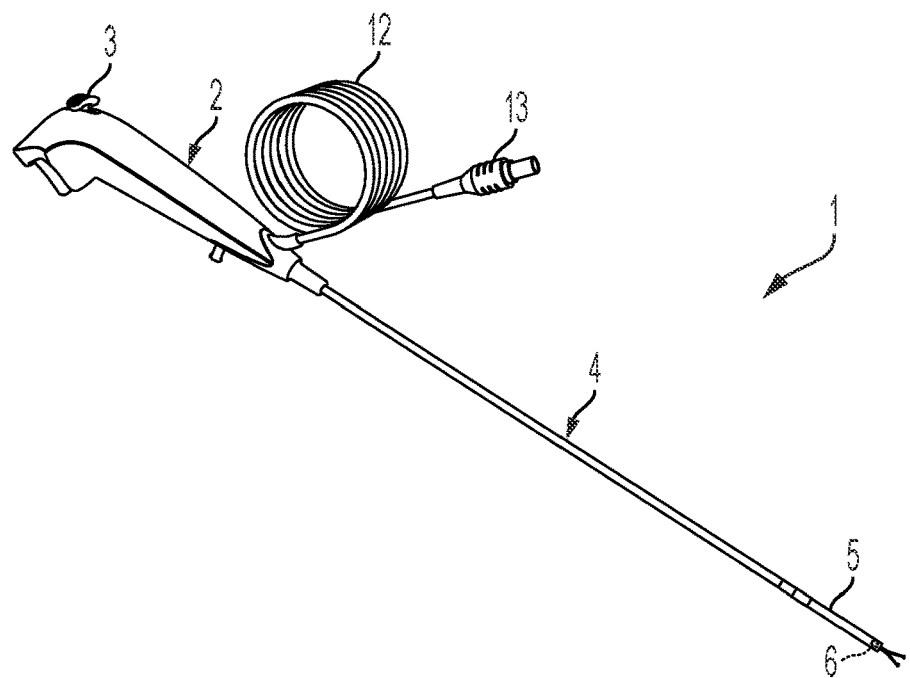
FIG. 1 is a perspective view of an embodiment of a videoscope.

For the purposes of promoting an understanding of the principles of the disclosure, reference will now be made to the embodiments illustrated in the drawings, which are described below. The embodiments disclosed below are not intended to be exhaustive or limit the disclosure to the precise form disclosed in the following detailed description.

FIG. 1 is a perspective view of a videoscope 1 comprising a handle 2 with an articulation lever 3 and an insertion tube 4 having an articulation section 5 and an image sensor 6 disposed at a distal end thereof. The image sensor captures optical images and transmits image data corresponding to the images via a cable 12 to a connector 13. Connector 13 is insertable into a connector port of a VPA to present graphical images corresponding to the optical images with a display module removably connected to the VPA. Movement of articulation lever 4 reorients the field of view of image sensor 6.

Figure 2:
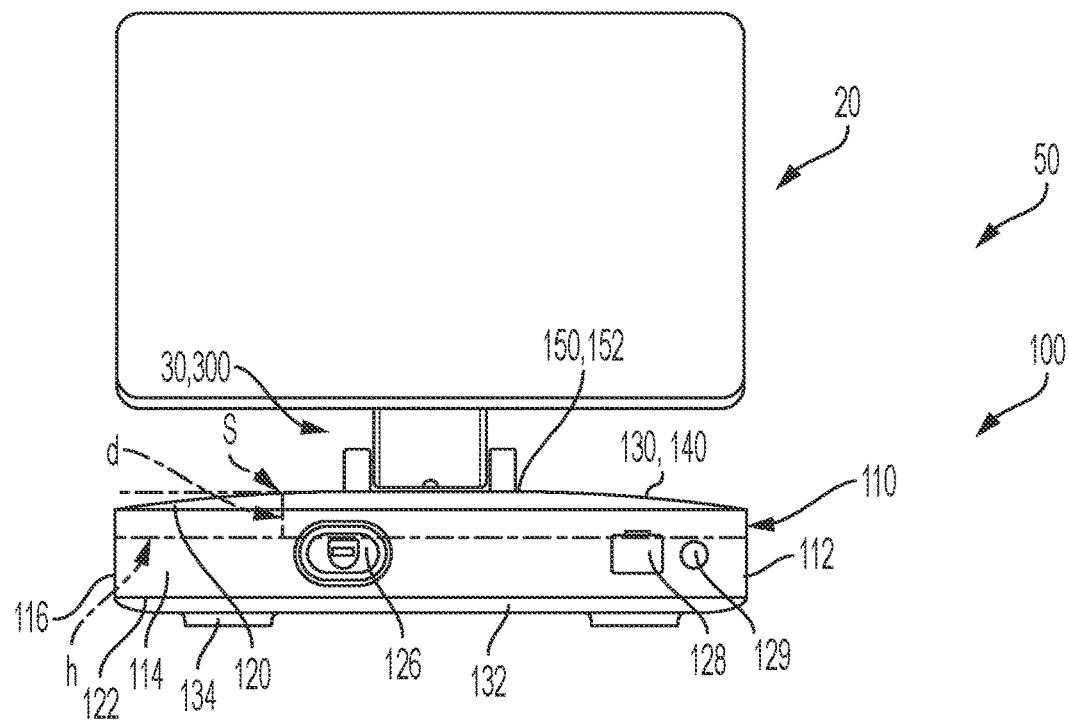
FIG. 2 is a perspective view of an embodiment of a video processing system including a video processing apparatus.
Figure 3:
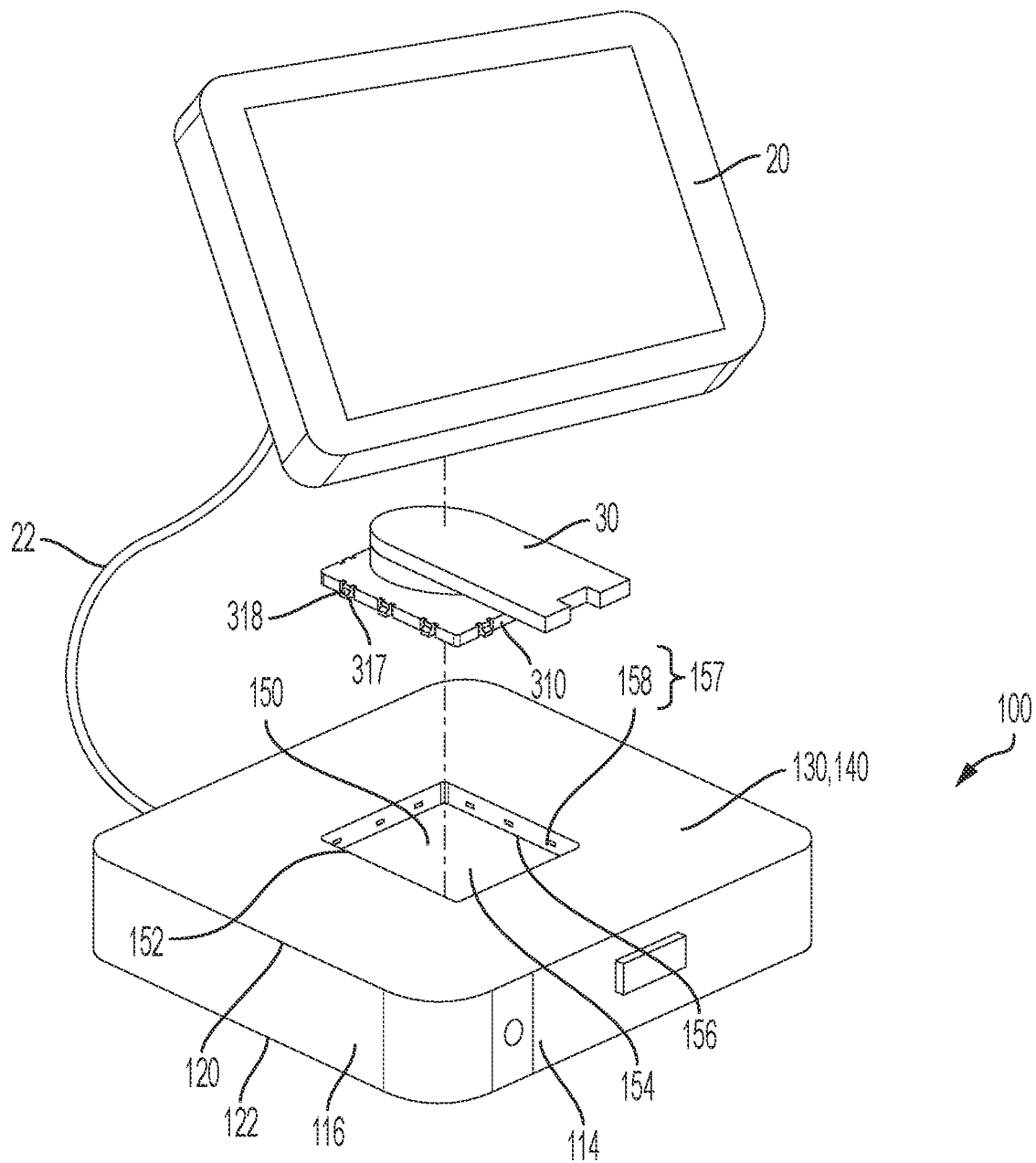
FIG. 3 is a perspective exploded view of another embodiment of a video processing system including a video processing apparatus.

FIG. 2 is a front view of a video processing system 50 including a VPA 100 connected to a display module 20 with a support bracket 30 and a cable 22 (shown in FIG. 3). VPA 100 has a housing 110 including lateral walls 112, 114, 116, 118 (best seen in FIG. 4) defining an upper periphery 120 opposite a lower periphery 122, a top wall 130, a bottom wall 132, and a number of standoffs 134 extending downwardly toward a support surface to elevate VPA 100 above the support surface. As shown, upper periphery 120 and lower periphery 122 extend from and between lateral walls 112, 114, 116, 118. An input port 126 is adapted to receive video input signals from connector 13 of videoscope 1. Video processing circuits (not shown) may combine the video input signals with user instructions and the resulting video output signals may be presented with a graphical user interface with display module 20. A USB port 128 is provided to facilitate connection to a portable storage device, e.g. USB memory. The portable storage device can be used to store images or video or to transfer device settings. A power button 129 activates a switch that enables power flow to the video processing circuits, as is known in the art. VPA 100 may alternatively have input ports located on the back wall (lateral wall 118) of housing 110 or a wireless interface to receive images wirelessly from videoscopes having wireless transmitters.

Top wall 130 has a top surface 140 that is curved and therefore elevates a bracket interface periphery 152 of a bracket interface 150 (discussed below) above upper periphery 120. Line h is a horizontal line representing a horizontal plane. Line s is a line parallel to line h. At any point at which lines touches top surface 140 there is a distanced between lines h and s. In some embodiments, the distance d decreases from bracket interface periphery 152 to upper periphery 120, reflecting a decreasing elevation, which allows fluids spilled onto top surface 140 to drain away from a bracket interface 150 and thus not penetrate into housing 110, to protect the video processing circuits therein.

Bracket interface 150 extends to bracket interface periphery 152. Top surface 140 extends, therefore, from upper periphery 120 to bracket interface periphery 152. Bracket interface periphery 152 is elevated relative to upper periphery 120, therefore top surface 140 exhibits a downward grade between bracket interface periphery 152 and upper periphery 120. A portion of top surface 140 surrounding bracket interface periphery 152 and/or upper periphery 120 may be horizontal, or parallel with the support structure, therefore the downward grade does not need to begin at bracket interface periphery 152 or end at upper periphery 120. The downward grade may be symmetric or asymmetric, curved or straight, and if curved concave or convex. Accordingly, although top surface 140 functions to cause fluids to flow away from bracket interface 150, portions of top surface 140 are non-functional and therefore may be selected based on their ornamental appeal. For example, top surface 140 functionally must have a bracket interface periphery 152 that is elevated relative to upper periphery 120, but the shape of top surface 140 may take on many aesthetically pleasing ornamental forms and other forms.

Figure 7:
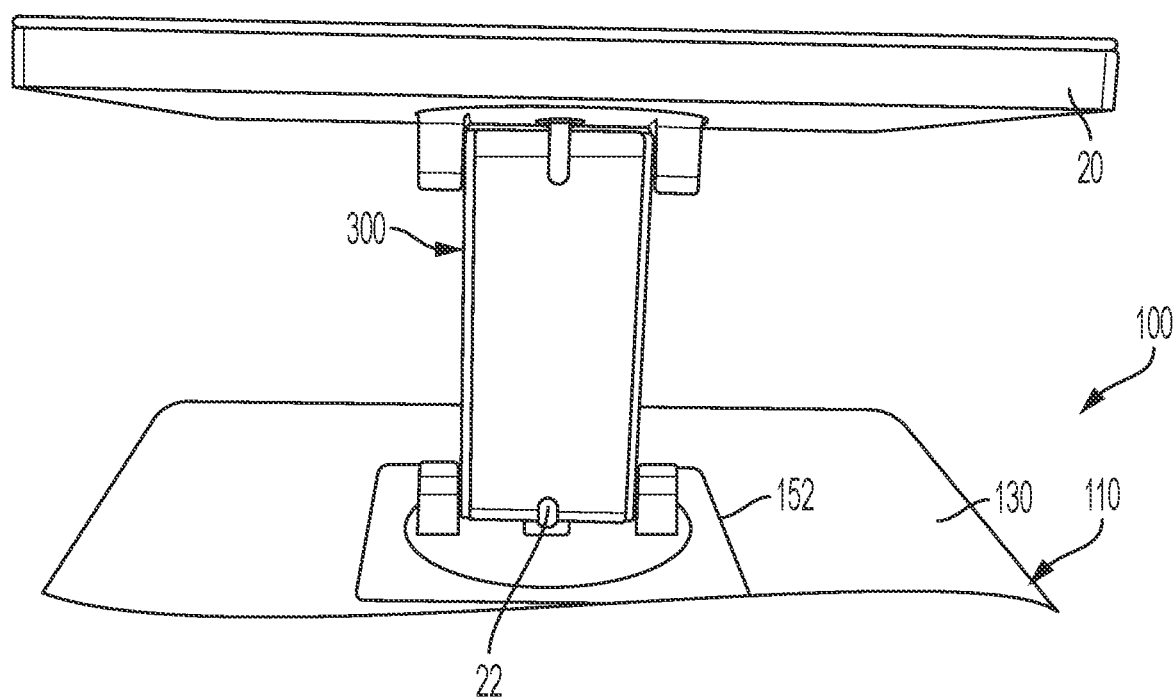
FIG. 7 is a partial perspective view of the embodiment of the video processing system of FIG. 2.

Referring to FIG. 3, housing 110 supports bracket interface 150. Bracket interface 150 comprises a plurality of walls 156 that define a bracket base receptacle 154 operable to receive a base end 300A, described further below. Walls 156 extend into an internal space 159 (shown in FIG. 13) located between the top, bottom and side or lateral walls of housing 110. Walls 156 may also extend outwardly or upward from top wall 130. Walls 156 include second retention features 157 sized and shaped to cooperate with first retention features 316 of support bracket 300 to removably retain support bracket 300 with bracket base receptacle 154, as described with reference to FIGS. 12 to 31. As shown, cable 22 is connected to a rear video output port 176 of VPA 100 (best seen in FIG. 5). Preferably, cable 22 is guided through bracket interface 150 and support bracket 300 and therefore is substantially invisible to the user, as shown in FIG. 7.

Figure 12:
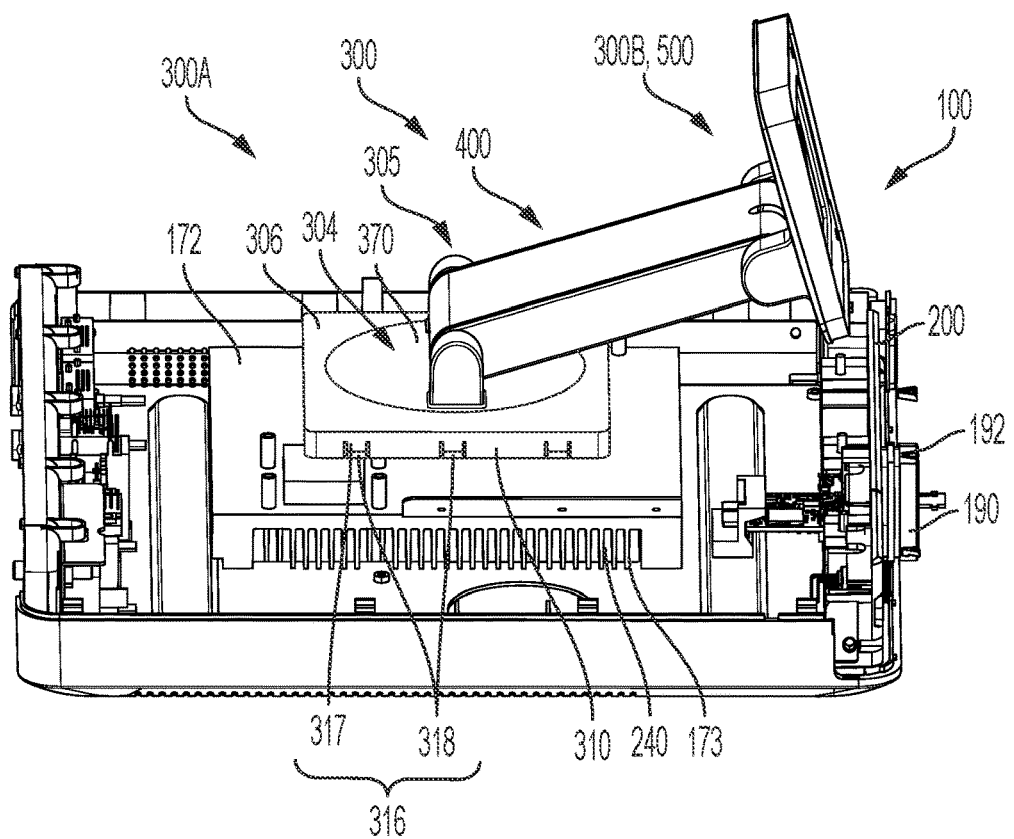
FIG. 12 is a further perspective view of the embodiment of the video processing system of FIG. 2 with a portion of the housing removed.

As shown, second retention features 157 comprise recesses 158 extending parallel to a length of each of walls 156 and first retention features 316 comprise protrusions 318 (shown in FIG. 12). Recesses 158 are operable to receive protrusions 318 to latch base end 300A of support bracket 300, as described below with reference to FIG. 12. The combination of protrusions and recesses form a biased retention mechanism including first and second retention features. In alternative embodiments, the biased retention mechanism, and thus first and second retention features, may comprise recesses and protrusions arranged in different ways, for example walls 156 may include the protrusions and base end 300A may include the recesses. Recesses 158 are shown as elongate or rectangular indentations but can also be square, circular, or comprise any other shape that can releasably couple a corresponding protrusion. Protrusions may comprise spring biased balls retained in semi-spherical cavities. The first and second retention features may each comprise one or a plurality of features and the features in each of the first and second retention features do not have to be the same or identical. A wall can, for example, include a combination of protrusions and recesses. Opposing walls can have protrusions while orthogonal walls include recesses. As shown, a swivel assembly of support bracket 30 is located above top surface 140.

Figure 4:
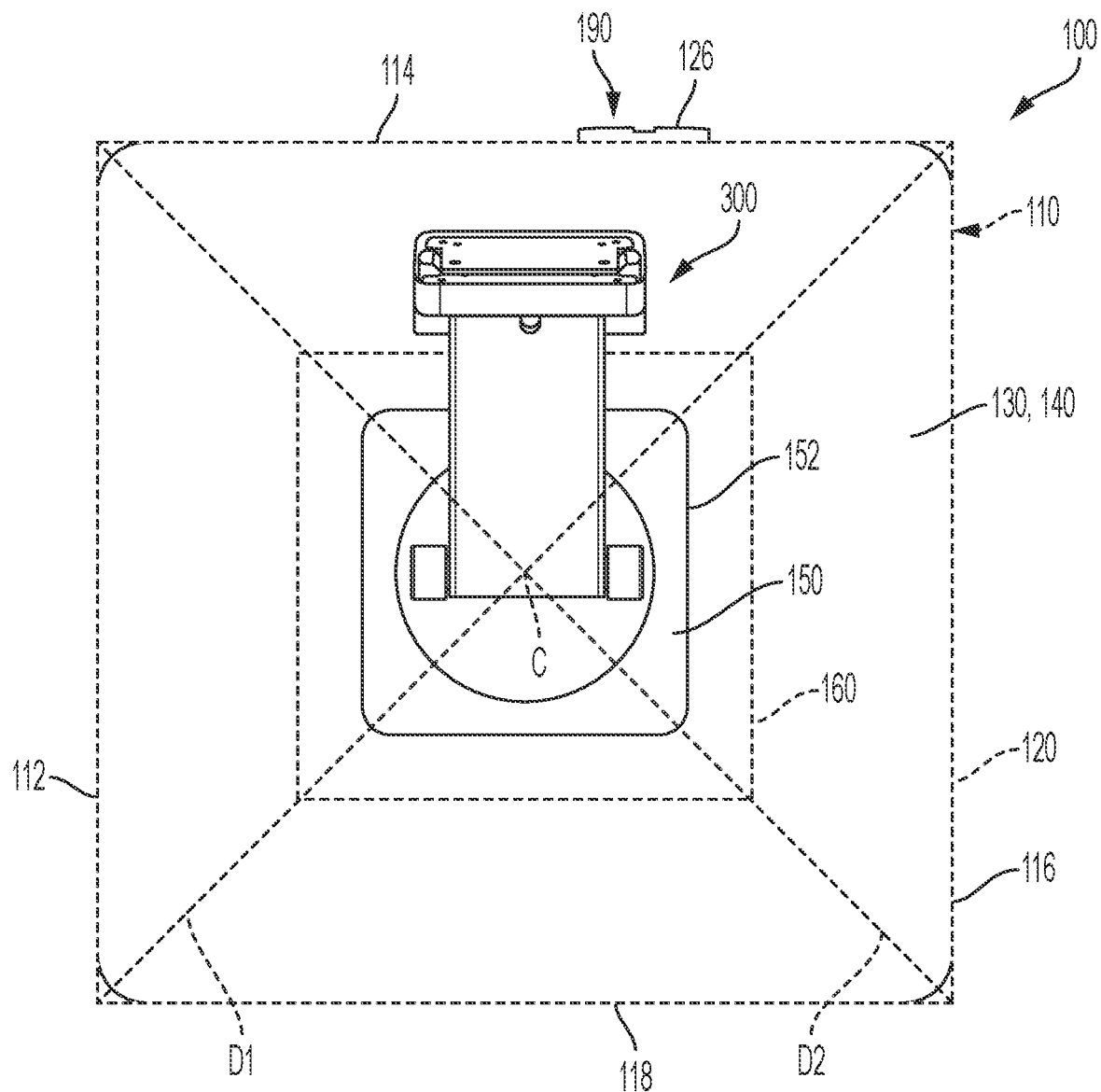
FIG. 4 is a top view of the embodiment of the video processing apparatus of FIG. 2.

FIG. 4 is a top view of VPA 100 and bracket 30, 300. Bracket 30 refers to brackets generically while bracket 300 denotes an embodiment of bracket 30. As shown, VPA 100 includes housing 110 having top wall 130 spaced apart from bottom wall 132, top wall 130 having top wall periphery 120, top surface 140 extending to top wall periphery 120, and a central area 160 within top wall periphery 120. Central area 160 refers to an area centered on point C, which is the center of top wall 130. In the case of a square or rectangular housing 110, as shown, point C is located at the intersection of diagonal lines D1 and D2. In the case of a circular housing 110, point C refers to the center of the circle. Other housing shapes are also contemplated. Central area 160 is shown to be larger than bracket interface periphery 152, therefore bracket interface 150 can, but does not have to be, centered on the top wall, and still be positioned within central area 160. Central area 160 may be at most ¾, ½, ⅓, or ¼ of the surface area of top surface 140, depending on the size, weight, and structure of housing 110 and display module 20, and may comprise the same peripheral shape as top surface 140. As shown, central area 160, which encompasses the horizontal area within bracket interface periphery 152, is less than about ⅓ of the surface area of top surface 140. The area of bracket interface periphery 152 should be large enough to provide a stable foundation for the display module while still allowing top surface 140 to exhibit a downward grade sufficient to drain liquids. A width of VPA 100 and housing 110, extending from lateral wall 112 to lateral wall 116, may greater than 60%, 70%, 80%, 90%, 100%, and 110% of the width of display module 20.

In some embodiments, input port 126 is adapted to receive video input signals from videoscope 1. A video output connector 229 (shown in FIG. 11) is adapted to transmit video output signals corresponding to the video input signals and adapted for presentation with display module 20. Video output connector 229 can be any connector operable to receive a mating connect of cable 22, to enable disconnection of cable 22 and placement of a cover (shown as 306A in FIG. 4A) in bracket base receptacle 154 if VPA 100 is to be used, for example, with a display module mounted on a wall, IV pole or set on a surface but not supported by VPA 100. Bracket interface 150 is supported by housing 110 and adapted to attach support bracket 30, 300 and to support display module 20 with support bracket 30, 300, bracket interface 150 being located within central area 160 of the top wall 130. An optional flexible connector ring 190 (described with reference to FIGS. 8 and 9) surrounds and protects input port 126.

In some variations of the present embodiment, top surface 140 extends convexly between bracket interface periphery 140 and top wall periphery 120. Top surface 140 may extend convexly from bracket interface periphery 140 to top wall periphery 120. Top surface 140 may extend convexly from bracket interface periphery 140 to two opposed lateral walls of housing 110, for example exhibiting the convexity on both sides of top surface 140 extending from a centerline, either front to back or side-to-side. Top surface 140 may extend convexly from bracket interface periphery 140 to all four opposed lateral walls of housing 110, for example exhibiting the convexity on both sides of top surface 140 extending from a front-to-back centerline and also on both sides of top surface 140 extending from a left-to-right centerline.

In some variations of the present embodiment, top surface 140 extends convexly from bracket interface periphery 140 to top wall periphery 120.

In some variations of the present embodiment, top surface 140 extends in a continuous manner from the bracket interface periphery to the top wall periphery.

Figure 4A:
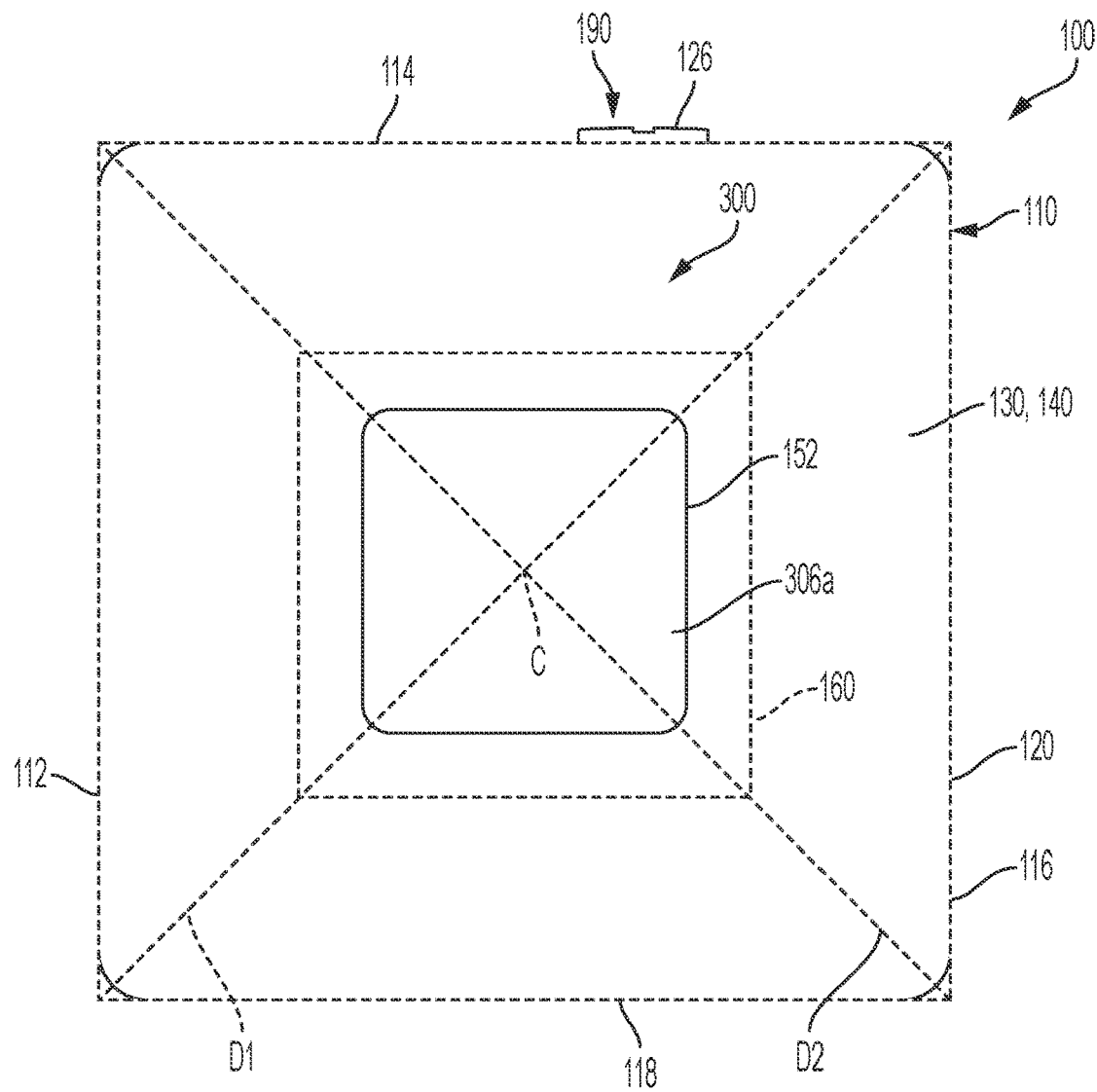
FIGS. 4A and 4B illustrate the video processing apparatus of FIG. 2 including a blank cover as shown in FIG. 4B.
Figure 4B:
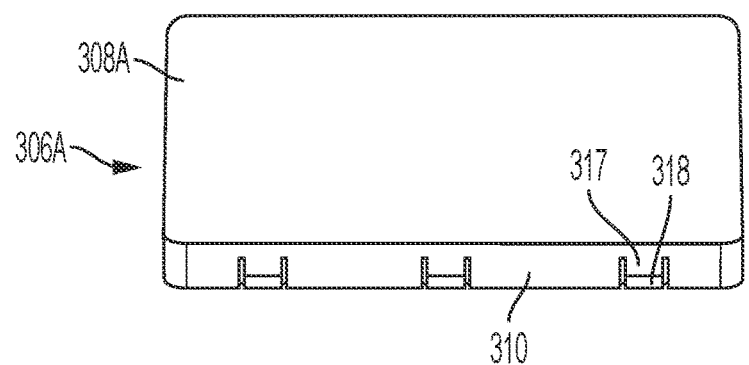
Figure 5:
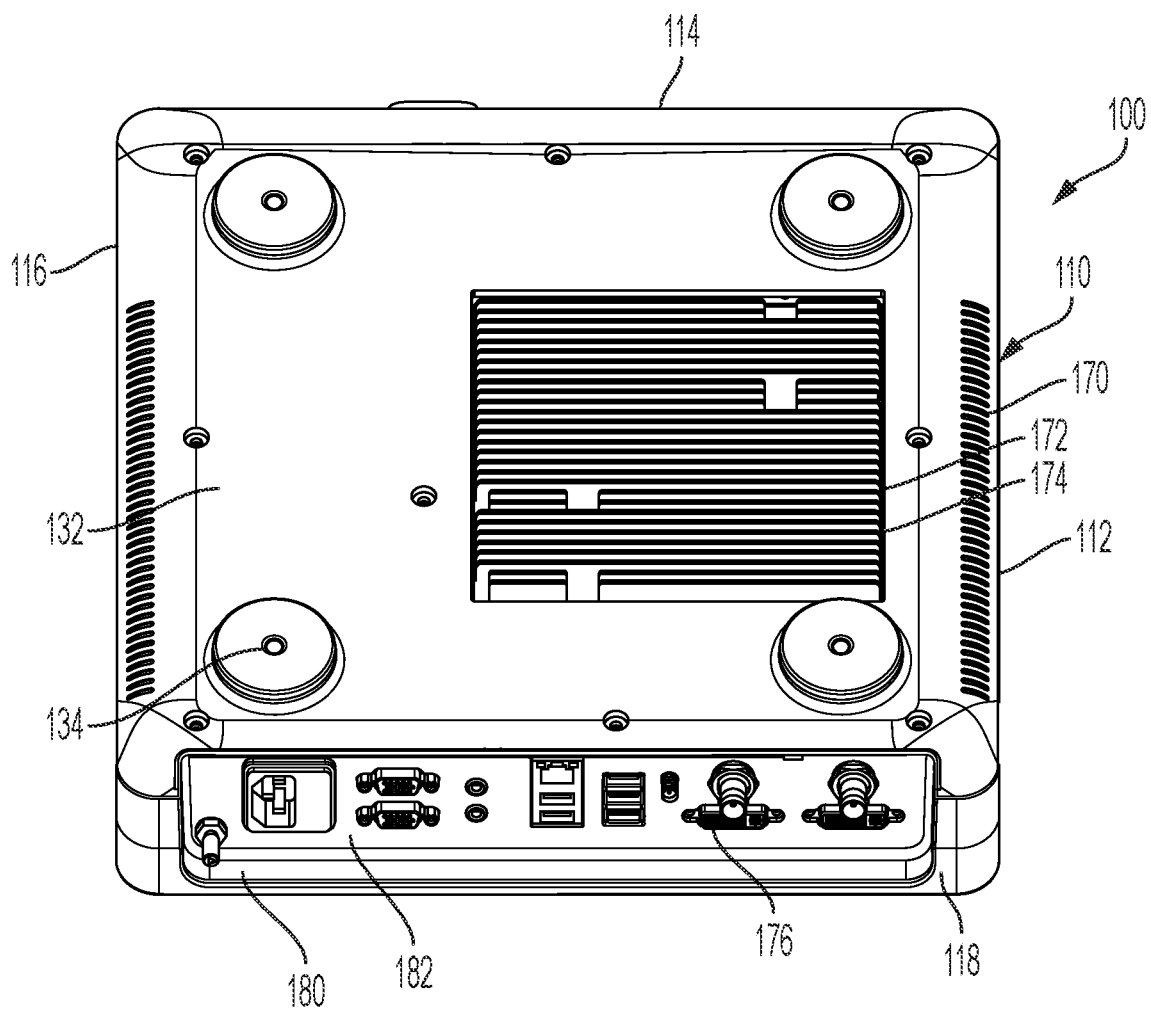
FIG. 5 is a perspective bottom view of the embodiment of the video processing apparatus of FIG. 2 showing a heat sink.

FIGS. 4A and 4B illustrate VPA 100 without bracket 300. Instead, a blank cover 306A is shown, including a top surface 308A. Cover 306A is operable to removably latch onto bracket interface 150 by insertion of wall 310, including first retaining features, into bracket base receptacle 154, including second retaining features, as described with reference to FIG. 12. In this manner the user can latch support bracket 300 or exchange support bracket 300 for another support bracket or for blank cover 306A using the first and second retaining features. As shown in FIGS. 5 and 26, wall 118 or a support frame recessed from it, include a video out port 176 in addition to USB ports. Video output port 176 can be used to connect an auxiliary monitor/display (not shown) to show the live images. Video output port 176 can be used in addition to and together with display module 20. When used in addition to display module 20, the auxiliary monitor may show the live image while display module 20 shows a GUI generated by graphical user interface logic 224 (described below). When used without display module 20, the auxiliary monitor may then show the live image and the GUI. The auxiliary monitor may comprise a touch sensitive display. Processor 220 detects the connection of various display modules and auxiliary monitors, as is known in the art, and is programmed to present different views, as described, depending on each predetermined configuration.

Figure 6:
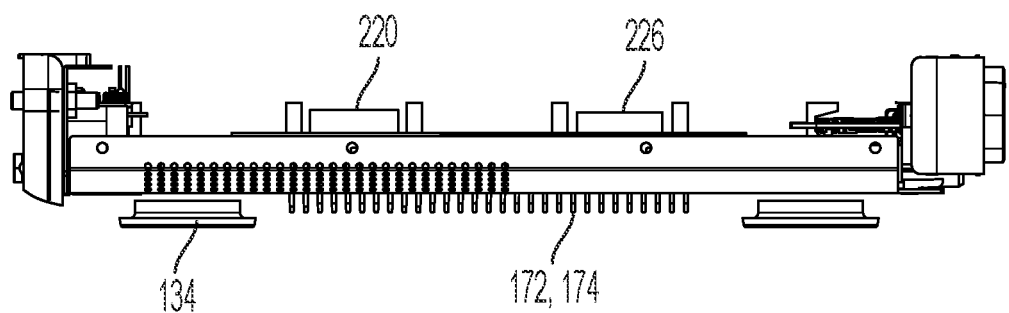
FIG. 6 is a side view of a portion of the video processing apparatus of FIG. 5.
Figure 11:
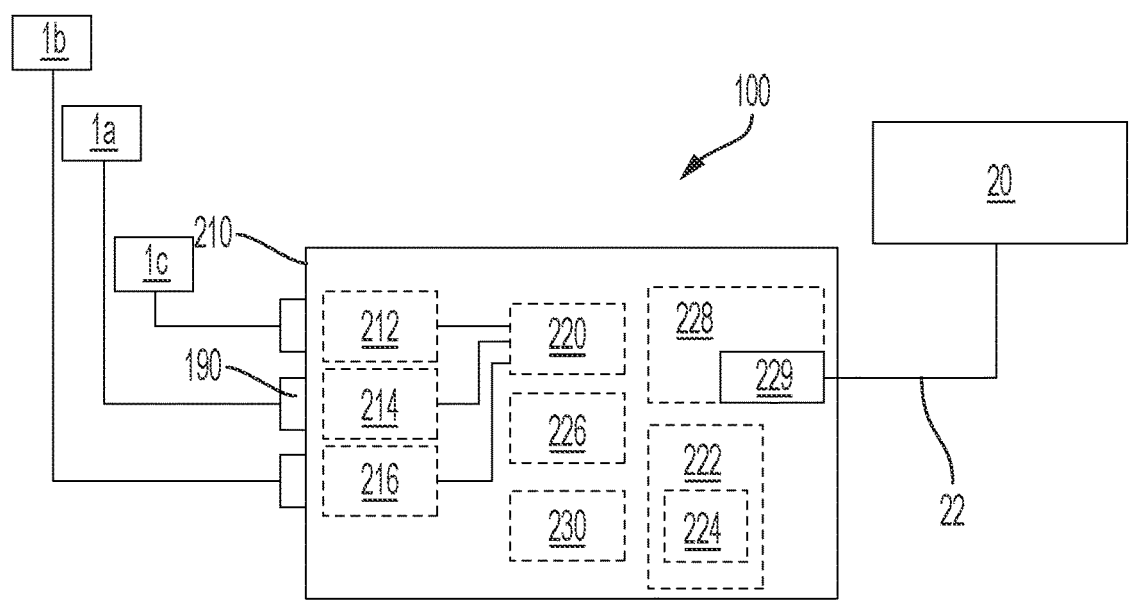
FIG. 11 is a block diagram of an embodiment of the video processing system.
Figure 13:
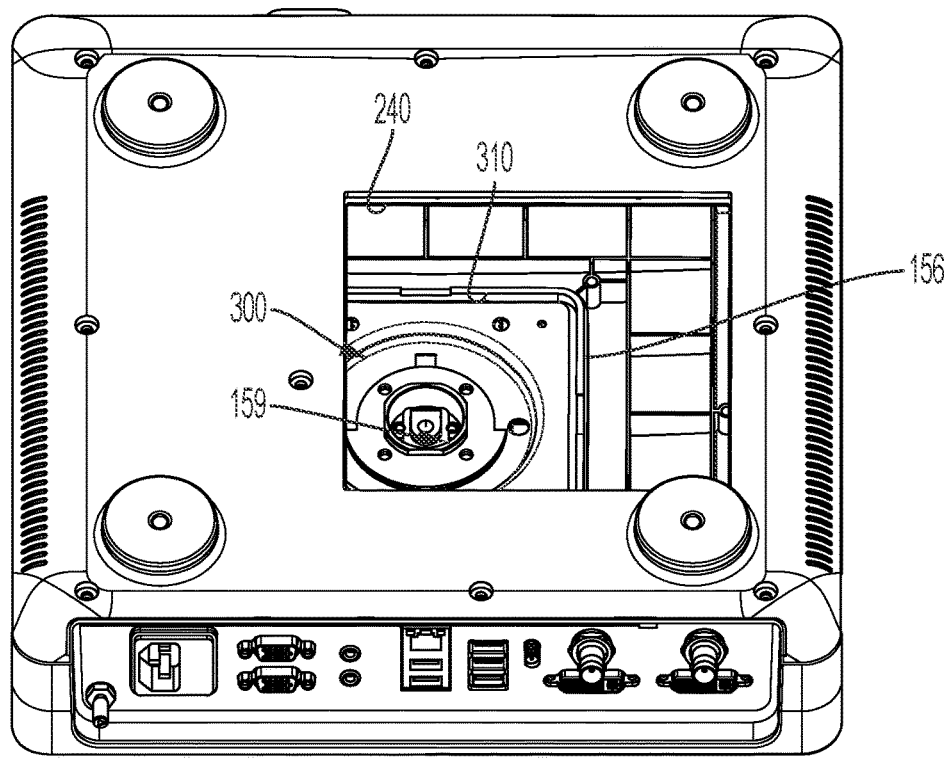
FIG. 13 is a perspective bottom view of the embodiment of the video processing apparatus of FIG. 2 with the heat sink removed.

Referring to FIGS. 5 and 6, ventilation grids 170 are provided to circulate air either passively, without a fan, or actively, with a fan. A heat sink 172 extends downward through bottom wall 132 so that a plurality of fins 174 extend therethrough to outside internal space 159 and thereby increase cooling capacity, as is known in the art. Top wall 130 extends rearward further than bottom wall 132, thereby creating a rear recess 180 where a portion of top wall 130, denoted by numeral 182, overhangs. The overhang protects the connectors provided on the rear of housing 110, including a video output port 176, from liquids that may drip from top wall 130. Additional output and other ports are shown. USB ports may be provided for connection of user interfaces, such as keyboard and mouse, as described below with reference to FIG. 11, for connection of USB storage, or for any known uses of devices with USB connectors. Display module 20 may comprise a touch-screen operable in a known manner to interact with a graphical user interface presented therein. A processor 220 and a field-programmable gate array 226, described below with reference to FIG. 11, are shown mounted onto heat sink 172. Processor 220 and field-programmable gate array 226 are electrically connected to a circuit board 210 positioned above them and due to the processing of instructions generate most of the heat generated by VPA 100. Accordingly, placing processor 220 and field-programmable gate array 226 on heat sink 172 may enable passive cooling. As shown in FIG. 13, heat sink 172 is positioned below and overlaps vertically with bracket interface periphery 152. Due to its weight, placing heat sink 172 on the bottom wall, below bracket interface periphery 152, stabilizes VPA 100, which is desirable to enable placement of display module 20 in various positions. As used herein, substantially denotes at least 60% and preferably 70%. In some examples, bracket interface periphery 152 overlaps substantially over heat sink 172. In some examples, bracket interface periphery 152 overlaps 40-50% over heat sink 172, e.g. 40-50% of the area of bracket interface periphery 152 is vertically over heat sink 172. Of course, heat sink 172 can have other shapes or be divided into more than one part, and thus the overlap can also be less than 40%.

FIG. 7 shows how cable 22 passes from internal space 159 through support bracket 300 to monitor 20.

Figure 8:
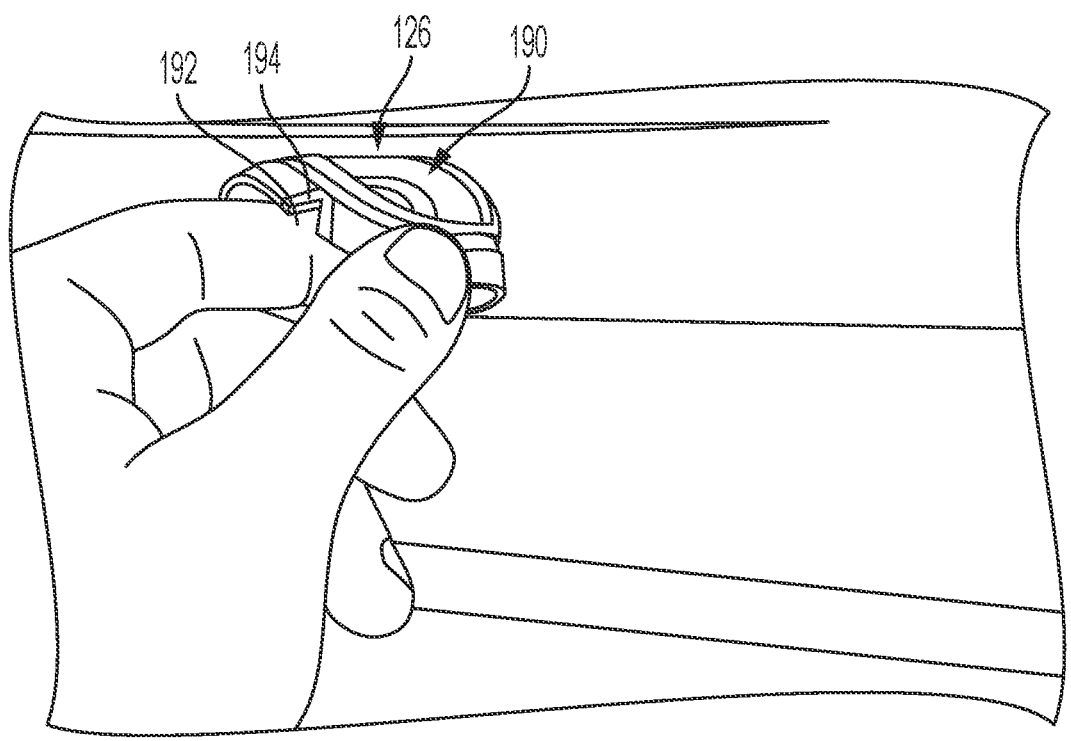
FIG. 8 is a partial perspective view of the embodiment of the video processing apparatus of FIG. 2 showing a connector ring.
Figure 9:
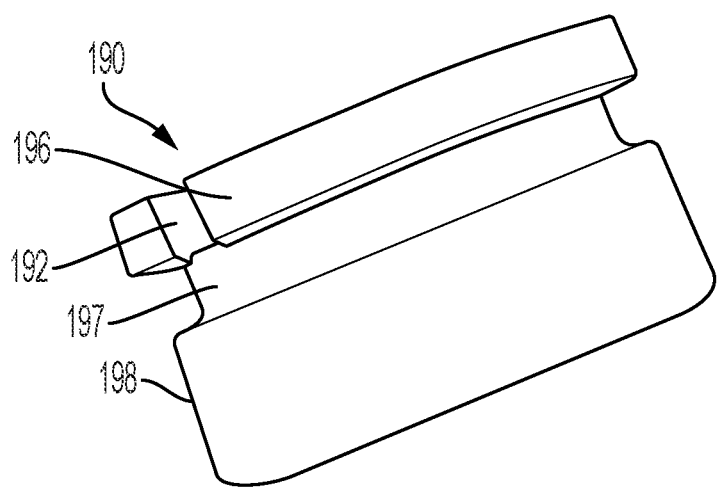
FIG. 9 is a perspective view of the connector ring of FIG. 8.

FIGS. 8 and 9, show a connector ring 190 comprising a plug hood 196, an intermediate portion 197, and a retention portion 198. The connector ring is mounted on an opening 204 in a wall of a support frame 200, e.g. cutout 204 (best seen in FIG. 10). The retention portion and the plug hood are larger in cross-section than the opening in the wall of the housing in at least one radial extent, and the intermediate portion is smaller in cross-section than the opening in the wall of the housing in the at least one extent, therefore the flexible material of the connector ring can be bent to pass the connector ring through the opening until the intermediate portion traverses the opening, at which time the plug hood and the retention portion secure the connector ring in the opening.

Plug hood 196 includes an alignment indicator 192, which may be, as shown, a notch shaped as the letter V. At least plug hood 196 is made from a flexible material. In the present embodiment, the connector ring is made from the flexible material, for example silicone or an elastomeric polymer. The connector ring may be molded or machined. Flexibility facilitates insertion of the cable connector, or plug, through the plug hood into the connector of a medical device interface. Additionally, flexibility prevents damage to the plug hood in case VPA 100 is accidentally dropped or hit. Thus, because the plug hood will not be damaged by contact, it can extend further than prior art plug hoods. Additionally, flexibility facilitates "blind" (by feel, without looking) insertion of a cable connector through plug hood 196 for coupling with a connector of a videoscope. Altogether, the tactile and visual alignment indicators facilitate visual and blind connections, as desired, which can be made more quickly than without the indicators.

The notch of alignment indicator 192 may be surrounded by a frame 194 of material of a color different than the color of the remainder of the connector ring to highlight the position of the notch. For example, frame 194 may be white while connector ring 190 may be blue, green, or another color.

Figure 10:
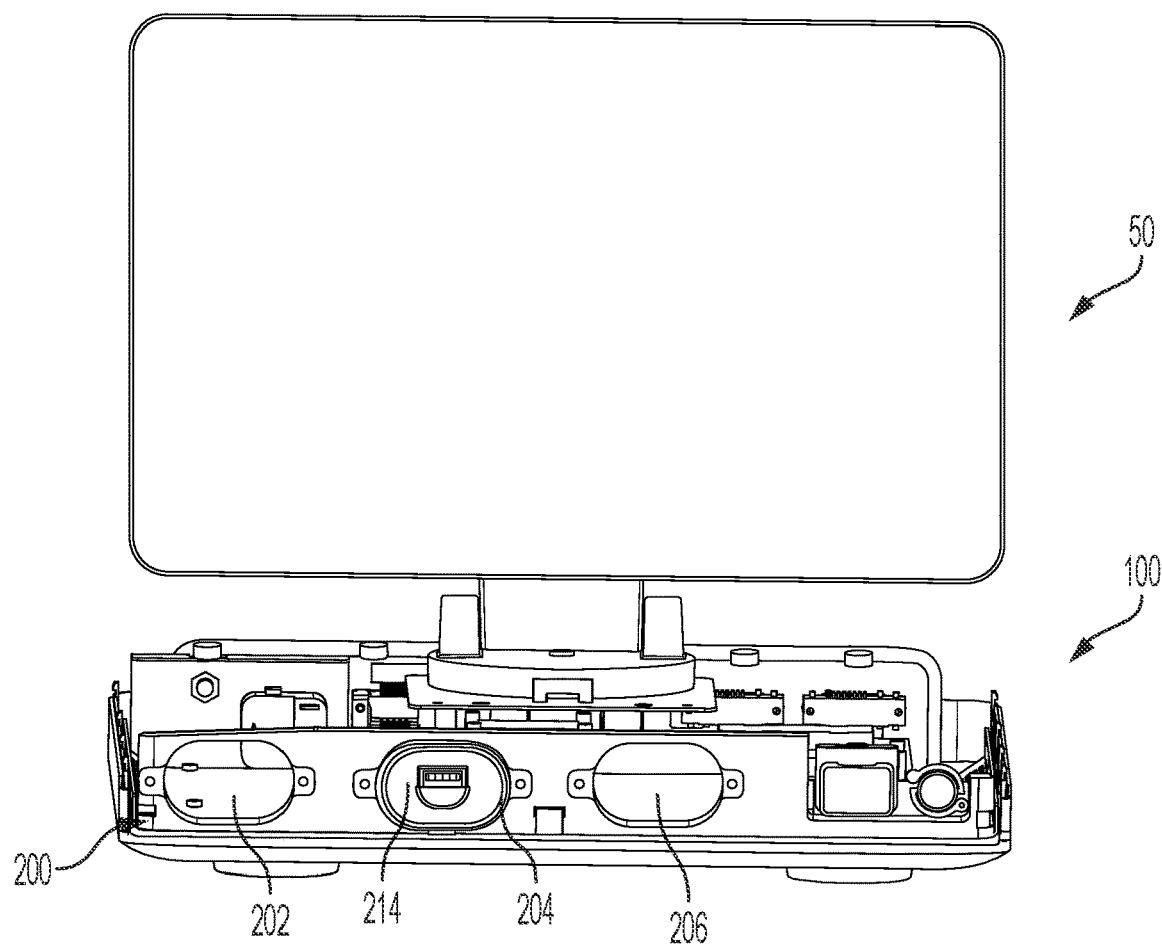
FIG. 10 is another partial perspective view of the embodiment of the video processing system of FIG. 2 with a portion of a housing removed.

FIG. 10 is another partial perspective view of the embodiment of the video processing system of FIG. 2 and FIG. 11 is a block diagram of an embodiment of the video processing system. VPA 100 includes a frame 200 including openings, or cutouts, 202, 204, and 206 and supported by housing 110. A video interface circuit 214 is positioned in internal space 159 with a port visible through cutout 204. Additional video interface circuits 212 and 216 may be positioned in the internal space with a port visible through cutout 202 and 206, respectively. Advantageously, the video interface circuits can be changed to match the technology of a respective videoscope. The color of connector ring 190, which fits in cutouts 202, 204, and 206, may be changed to match the respective technology and indicate where one of multiple videoscopes, e.g. 1a, 1b, 1c, should be connected for proper operation.

VPA 100 includes a processor 220, memory 222 including graphical user interface (GUI) logic 224, a field-programmable gate array (FPGA) 226, and a video output board 228 including video output connector 229. VPA 100 may also include a microphone, a wireless interface operable to receive user inputs via a mouse, keyboard, or other physical user input devices. Example wireless interfaces include Bluetooth and Zigbee controllers. A user interface 230 may also comprise a USB port to receive a USB connector of a wired user input device. Thus, VPA 100 provides for flexibility in receiving user inputs via various user input devices. A circuit board 210 comprising one or more rigid circuit board parts may be provided to mount some or all of the electronic devices, including processor 220 and FPGA 226. Memory 222 may also be mounted thereon, for example.

FPGA 226 is optionally provided because it is capable of rapid power-up (i.e. short boot-up time) and thus is useful in emergency situations. FPGAs may also be provided in the medical device interfaces for the same reasons. FPGAs process data very fast compared to other memory/instruction combinations and are re-programmable. Therefore, FPGAs facilitate presentation of a live view of the images captured by the videoscope in real-time with minimal latency so that the physician observing the live view can take immediate actions even in emergency situations. As technology evolves, the functionality of FPGA 226 may be combined with processor 220. VPA 100 is therefore not limited to the precise packaged integrated circuits described with reference to FIG. 11 but can be constructed to take advantage of design and cost targets and future video processing technologies. For example, faster/more costly memory may be used to increase graphics processing speed. Graphics processing may be provided in the FPGA or a processor that incorporates graphics processing logic may be used instead.

The term "logic" as used herein includes software and/or firmware executing on one or more programmable processing devices, application-specific integrated circuits, field-programmable gate arrays, digital signal processors, hard-wired logic, or combinations thereof. Therefore, in accordance with the embodiments, various logic may be implemented in any appropriate fashion and would remain in accordance with the embodiments herein disclosed. Logic may comprise processing instructions embedded in non-transitory machine-readable media (e.g. memory).

GUI logic 224 comprises processing instructions to generate a GUI presented with display module 20. The GUI can be responsive to user inputs received via the touch screen or other user inputs. Processor 220 receives image data from medical device interfaces 212, 214, and 216 and outputs video signals incorporating the GUI and image data. Image data may be referred to "live images" or "live video" if they are received substantially in real-time from the videoscopes. The video signals may be received by a memory buffer and the buffer may be read by the display module or video output card to present the GUI and images. Techniques for presenting images are well known, including techniques using buffers or mapped memory. The GUI may comprise first and second panels provided side-by-side in a view. The second panel presents live images and is positioned on the right side of the view, with the first panel positioned on the left side of the view. The GUI may present in the first panel a small version of live images provided by a second videoscope and the user may use the GUI to switch the live images from the first and second videoscopes so that the images from the second videoscope are presented in the second panel while the images from the first videoscope are reduced and presented in the first panel. However, the views from the different videoscopes can be selected by the user with the GUI for presentation in the first or second panel or not displayed at all. The GUI may present various icons corresponding to actions selectable by the user with any of the above-described user input devices, to for example store a copy of a live image, store a portion of video corresponding to live images, invert the views, apply correction curves to the image data to reduce overexposure, etc.

Figure 15:
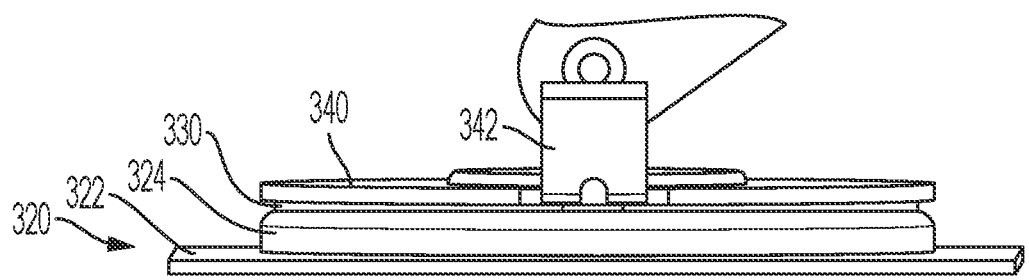
FIG. 15 is a side view of an embodiment of a swivel assembly of the video processing system of FIG. 2.
Figure 16:
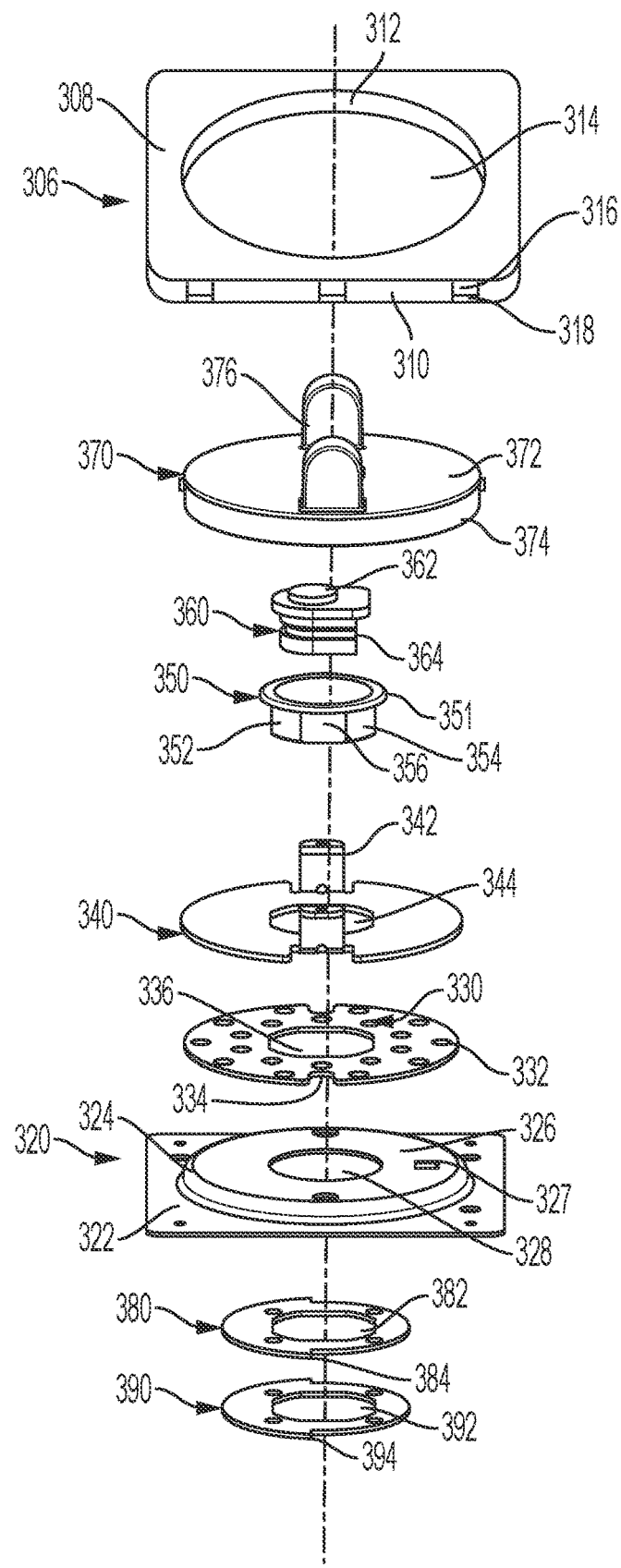
FIG. 16 is an exploded view of the swivel assembly of FIG. 15.

Turning attention now to FIGS. 12 to 31, support bracket 300 is shown in relation to portions of VPA 100. In FIG. 12, top wall 130 was removed to show heat sink 172. Fins 174 protrude through a through-hole 240 in bottom wall 132. A swivel base 306 of a swivel assembly 304 secures swivel assembly 304 to housing 110. FIG. 16 is an exploded view of swivel base 304.

Referring to FIG. 12, in some embodiments of video processing system 50, including VPA 100, support bracket 300 comprises a base end 300A opposite a display end 300B and an arm 400 extending between base end 300A and display end 300B.

Base end 300A includes first retention feature 316, and bracket interface 150, supported by housing 110, includes bracket base receptacle 154 and second retention feature 157, bracket base receptacle 154 sized and shaped to receive base end 300A of support bracket 300, and second retention feature 157 sized and shaped to cooperate with first retention feature 316 to removably retain base end 300A of support bracket 300.

Base end 300A includes a swivel assembly 304 operable to rotate arm 400 in a first dimension and display end 300B includes a first pivot assembly 500 operable to rotate in a second dimension different than the first dimension. The first and second dimensions correspond to planes perpendicular to first rotation axis 1AX and second rotation axis 2AX (shown in FIG. 14), typically provided by axles. Thus, the display module can swivel in one plane and pivot in another. The arm of the support bracket can pivot about the VPA and allow the display module to pivot about a third axis 3AX (shown in FIG. 14), both pivot motions potentially in the same dimension but about different pivot axis. As shown, swivel assembly 304 fits within bracket base receptacle 154. Display module 20 is connected to support bracket 300 by first pivot assembly 500. In FIG. 3, support bracket 30 may comprise swivel assembly 304 but may be constructed such that swivel assembly 304 is located outside bracket base receptacle 154. Display module 20 may be connected to support bracket 30 by first pivot assembly 500.

Base end 300A also includes a second pivot assembly 305 operable to rotate the arm in the second dimension.

In some variations, swivel assembly 304 comprises a swivel frame 320, a friction plate 330, and a pivot assembly support 340, friction plate 330 positioned between swivel frame 320 and pivot assembly support 340.

In some variations, friction plate 330 comprises a textured surface 332 configured to provide a predetermined amount of swivel resistance to swivel assembly 304.

Base end 300A includes swivel base 306 which is operable to latch onto bracket interface 150 by insertion of a wall 310 including tabs 317 into bracket base receptacle 154. Each of tabs 317 is connected to swivel base 306 near a top surface of swivel base 306 and has a width sized to permit each tab to resiliently bend so that protrusion 318 at its distal end (the end opposite the top surface) can enter through bracket interface periphery 152 causing tabs 317 to bend toward center C until swivel base 306 is fully inserted, at which time protrusions 318 mate with corresponding recesses 158 in walls 156 to removably latch swivel base 306, and accordingly support bracket 300, in bracket interface 150. In this manner support bracket 300 can be exchanged for another support bracket using the first and second retaining features, by pulling bracket 300 to unlatch it.

FIG. 13 is a perspective bottom view of VPA 110 showing that heat sink 172 is positioned below and substantially overlaps vertically with bracket interface periphery 152.

Figure 14:
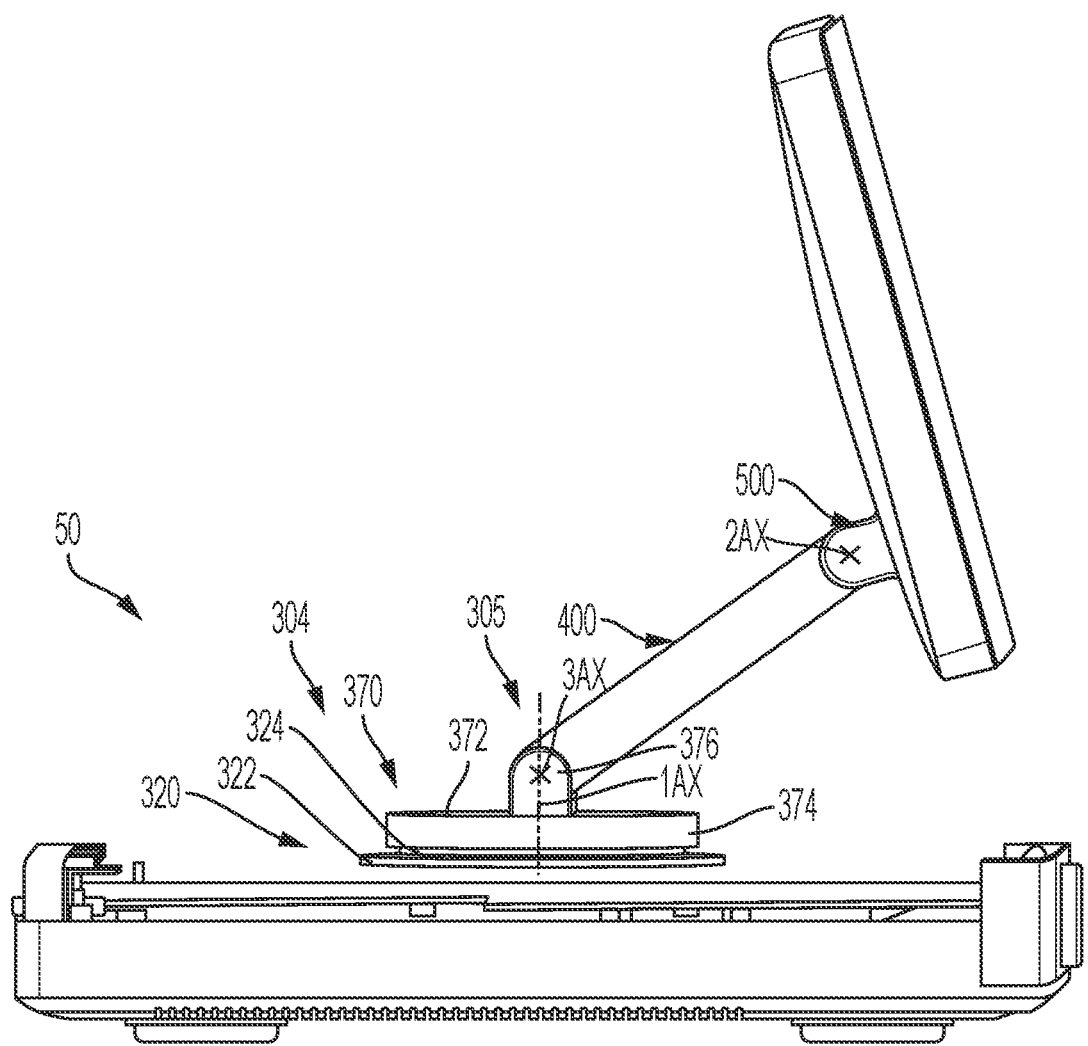
FIG. 14 is a yet further perspective view of the embodiment of the video processing system of FIG. 2 with a portion of the housing removed.

FIG. 14 is a side view of system 50 with top wall 130 and swivel base 306 removed to show additional details of base end 300A, including swivel assembly 304. FIG. 15 is a side view of swivel assembly 304 and FIG. 16 is an exploded view of swivel assembly 304.

Referring to FIG. 16, swivel assembly 304 comprises swivel base 306, swivel frame 320 supported by swivel base 310, friction plate 330, a pivot assembly support bushing 340, a swivel axle 350, and a swivel assembly cover 370.

Swivel base 306 includes a top wall 308, a side wall 310 extending inwardly from top wall 308, a circular wall 312 extending inwardly from top wall 308 and defining a through-hole 314, tabs 317, and protrusions 318.

Swivel frame 320 comprises a support plate 322 with a circular protrusion 324 extending upwardly therefrom and sized to fit within through-hole 314. Swivel frame 320 is stationary and can be attached to swivel base 306 with fasteners. Example fasteners include threaded fasteners, rivets, adhesive, snap connections and the like. Apertures for fasteners are shown on support plate 322. Circular protrusion 324 has a top wall 326 with a top surface on which friction plate 330 lies and rotates. Top wall 326 includes a stop feature 327, illustratively a protrusion, which together with position plates 380 and 390 (discussed below), limit the amount of swivel. Top wall 326 also includes a circular hole 328.

Friction plate 330 comprises textured surface 332 configured to provide a predetermined amount of swivel resistance to swivel assembly 304 by controlling the coefficient of friction of its surface(s). As shown, textured surface 332 comprises a plurality of dimples which in aggregate reduce the amount of contact surface. Alternatively, textured surface 332 can be coated with, for example, teflon, to reduce the coefficient of friction, or can include any other texturing, including circular grooves and protrusions. Friction plate 330 also includes a central aperture 336 with straight and arcuate sections, and a pair of alignment slots 334. The coefficient of friction of friction plate 330 is preferably less than the coefficient of friction of swivel frame 320 and pivot assembly support bushing 340.

Pivot assembly support bushing 340 includes second pivot assembly supports 342 comprising upwardly extending arms and laterally extending tabs, each tab having a hole therethrough. Pivot assembly support bushing 340 also includes a central aperture 344 with straight and arcuate sections.

Swivel axle 350 comprises a collar 351 and a shaft 352 comprising straight 356 and arcuate 354 sections. The shaft passes through apertures 344, 336, and 328. The straight sections of the apertures cooperate with the straight sections of the shaft so that the components rotate together. By contrast, the shaft passes through circular hole 328 and rotates therein without causing swivel frame 320 to rotate therewith.

A cable retainer 360 is shown having an aperture 362 and a shaft 364 configured to fit within a central aperture of swivel axle 350. Cable 22 can be retained by aperture 362.

Swivel assembly cover 370 comprises a top wall 372, a circular wall 374, and second pivot assembly support covers 376 which are sized to fit over second pivot assembly supports 342 when swivel assembly cover 370 is assembled. Swivel assembly cover 370 may be adhesively or otherwise bonded to collar 351 or an inner surface of top wall 372 can be shaped to receive collar 351 and then be bonded to a top surface of pivot assembly support bushing 340. Pivot axles 430 are inserted into apertures on support covers 376 and fastened to pivot assembly supports 342 on pivot assembly support bushing 340. Holes 436 may be threaded to allow fastening from below after insertion of pivot axles 430 into the apertures. Snap-fittings may also be used, for example, or any other suitable fastening means. Circular wall 374 is sized and shaped to fit within through-hole 314 and gap between them can be designed so that the surfaces glide, thereby providing additional stability to swivel assembly 304.

Swivel assembly 304 also includes one or more position plates 380, 390, each including an aperture 382, 392, respectively, and stop features 384, 394, which stop rotation of pivot assembly support bushing 340, and therefore of arm 400, when they contact stop feature 327. As disclosed, stop surface 327 can be a protrusion which extends downward from top wall 326 to make contact, at certain predetermined angles, with stop surfaces 384, 394.

Shaft 351 may be threaded and a nut may be used to secure the components of swivel assembly 304 together after they are assembled.

In use, swivel base 306 secures swivel assembly 304 to housing 110, and pivot assembly support bushing 340 supports second pivot assembly 305, which supports arm 400 and display module 20. Thus, when second pivot assembly 305 rotates, or swivels (together with swivel axle 350, friction plate 330, swivel assembly cover 370, and position plates 380, 390), display module 20 swivels along a dimension parallel to top surface 130 of housing 110.

Figure 17:
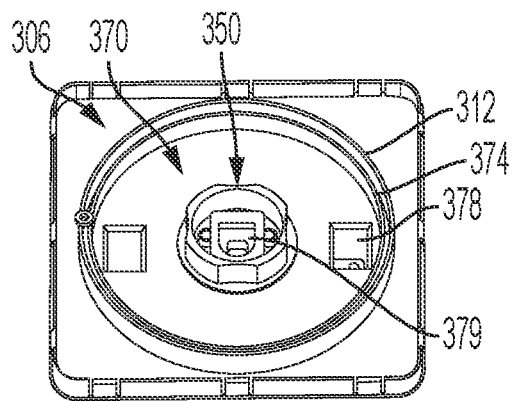
FIGS. 17 to 20 illustrate the swivel assembly of FIG. 15 in different assembly stages.
Figure 18:
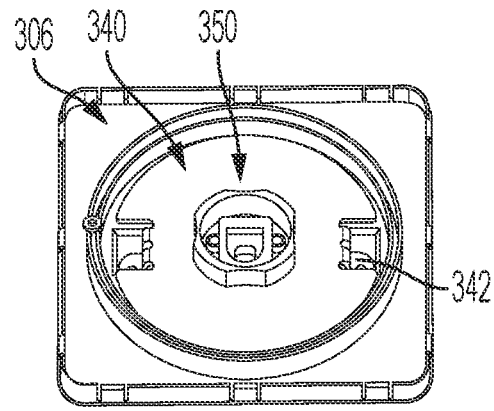
Figure 19:
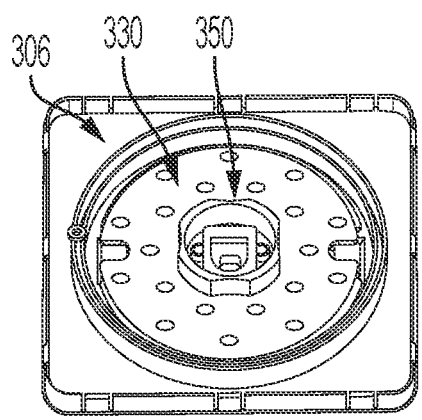
Figure 20:
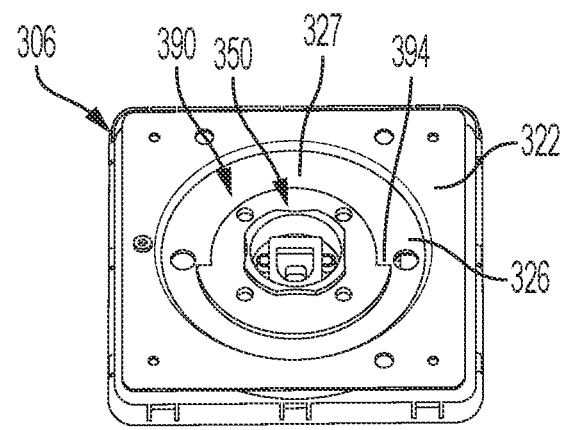

Assembly of swivel assembly 304 is illustrated reference to FIGS. 17 to 20. The figures illustrate sequential assembly steps of swivel base 306 and swivel axle 350 (FIG. 17), the addition of pivot assembly support bushing 340 (FIG. 18), the addition of friction plate 330 (FIG. 19), and the addition of swivel assembly cover 370 and position plates 380, 390 (FIG. 20). FIG. 17 shows also apertures 378 and 379, which are provided to facilitate retention of cable 22 and passage of second pivot assembly supports 342 through top wall 372 of swivel base 306.

Retainment of cable 22 through swivel assembly 304 gives system 50 a neat appearance by hiding the cable instead of the traditional approach of having a cable plugged into a connector at a lateral wall of the housing. Optionally, a connector inside housing 110 is provided to mate with the connector of the cable so that it can be removed. Having the cable protrude from a central through-hole allows rotation of the monitor around center C without necessitating extra cable, resulting in the neat appearance.

The swivel base secures the swivel assembly and the second pivot assembly to the housing. In some embodiments, the swivel base comprises a cylindrical tube with the first retention features. In some variations the swivel assembly is attached to the cylindrical tube as shown in FIGS. 16-20. In other variations the swivel assembly is attached to the cylindrical tube above the top surface of the housing.

In some embodiments, a cable and cable connector are included in the swivel base, whether as shown in FIG. 16 or described in the preceding paragraph, and a matching connector is included in the VPA, as previously described, sized and positioned in the VPA to mate with the cable connector when the swivel base is attached. Thus, when the swivel base is latched, the two connectors mate. The VPA connector may extend through the base of the receptacle and be sealed thereto with adhesives, coatings, bushings, compression fittings and the like, to provide a water-tight bracket interface.

In some embodiments, the bracket interface is omitted. Instead, the connector for the cable is provided accessible through the top surface. A bottom surface of the swivel base or the swivel assembly is shaped to match the top surface of the housing. The bottom surface can be provided by the support plate of the swivel assembly, which may be extended laterally to provide additional support. A silicone coating, rubber or other sticky substance may be applied to the bottom surface to help keep the swivel base in position.

In some embodiments, the bracket interface comprises first retention features on the top wall of the housing without forming a receptacle for the swivel assembly. The connector for the cable may be provided accessible through the top surface or on the rear wall, as described above. A bottom surface of the swivel base or the swivel assembly is shaped to match the top surface of the housing. The bottom surface can be provided by the support plate of the swivel assembly, which may be extended laterally to provide additional support. A silicone coating, rubber or other sticky substance may be applied to the bottom surface to help keep the swivel base in position. The bottom surface may include the second retention features to match the first retention features. The retention features may be made very small, combining an expanded bottom surface size and curvature to secure the bracket to the housing while still presenting an appealing top surface of the housing. Alternatively, the top wall of the housing can be provided with a "step" or discontinuity, e.g. a protruding surface with lateral walls, the lateral walls including or forming the first retention features, as described with reference to FIG. 3, for example.

In some embodiments, the bracket interface comprises multiple receptacles. Two three or four receptacles spaced apart over the top surface may be provided. Each receptacle may include first retention features. The swivel assembly is positioned above the top surface. The multiple receptacles secure the swivel assembly, for example via the support plate, to the housing.

Arm 400 will now be described with reference to FIGS. 21 to 31. With respect to VPA 100, arm 400 can be any arm of a support bracket known or future developed. Provision of two pivot assemblies enables movement of the display module up and down while maintaining a desired visualization angle relative to the face of the user. The pivot assembles are designed to maintain the desired position, therefore they contain a biasing component such as a spring component which can be any type of spring, including coils, elastomers, rubbers, and resilient metal plates, for example.

Figure 21:
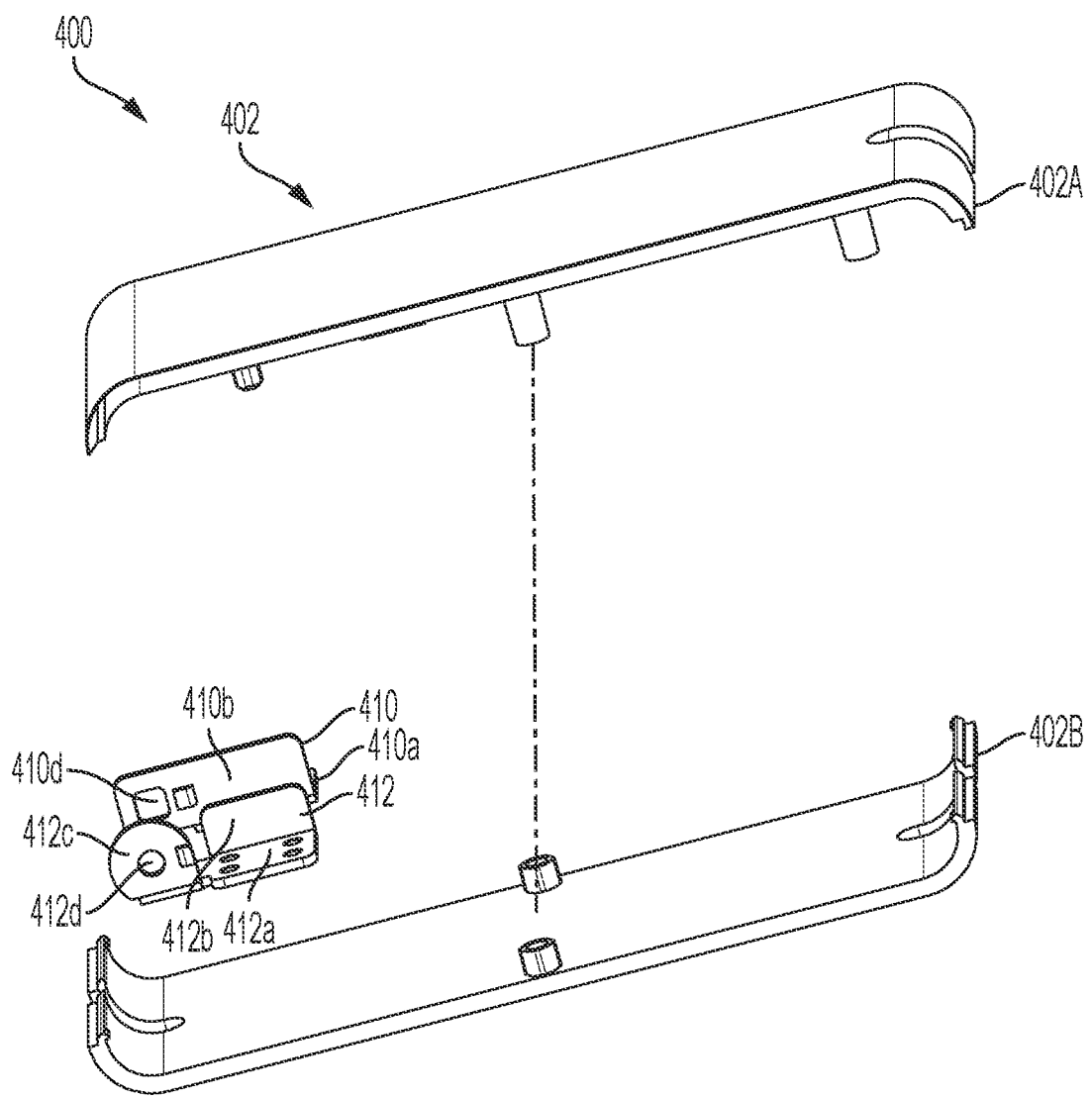
FIG. 21 is a partial exploded view of an arm of a support bracket.
Figure 22:
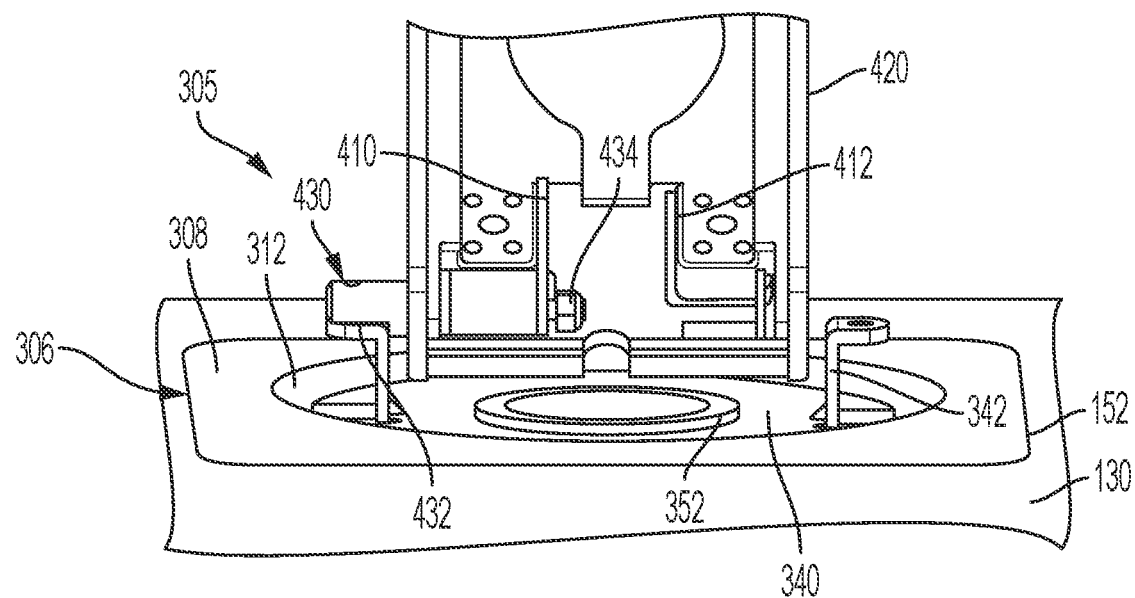
FIGS. 22 and 23 are partial perspective and top views of a pivot assembly of the embodiment of the video processing system of FIG. 2.
Figure 23:
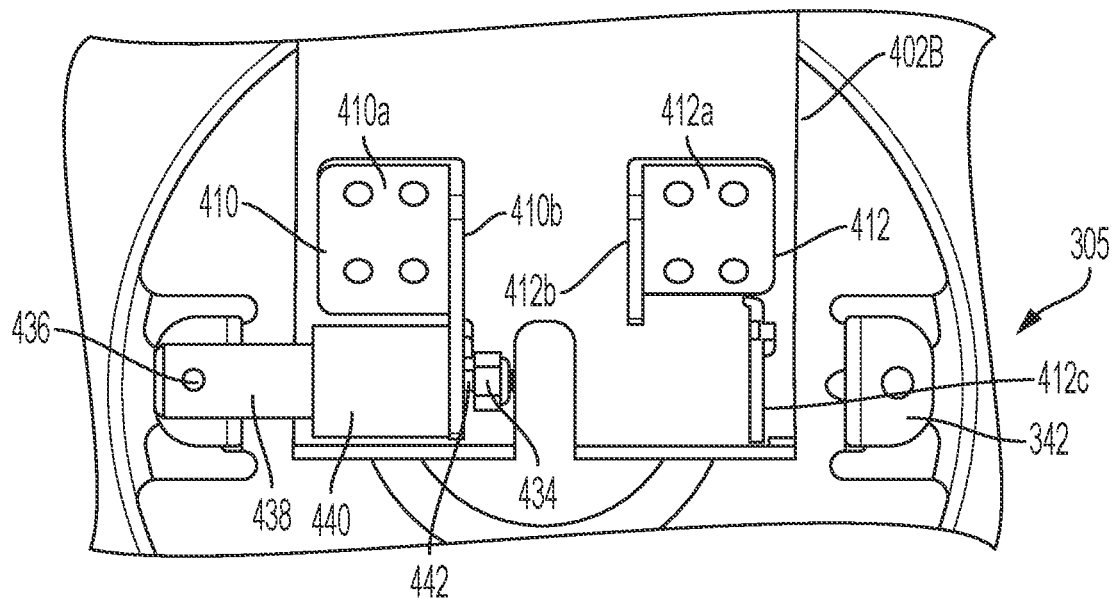
Figure 24:
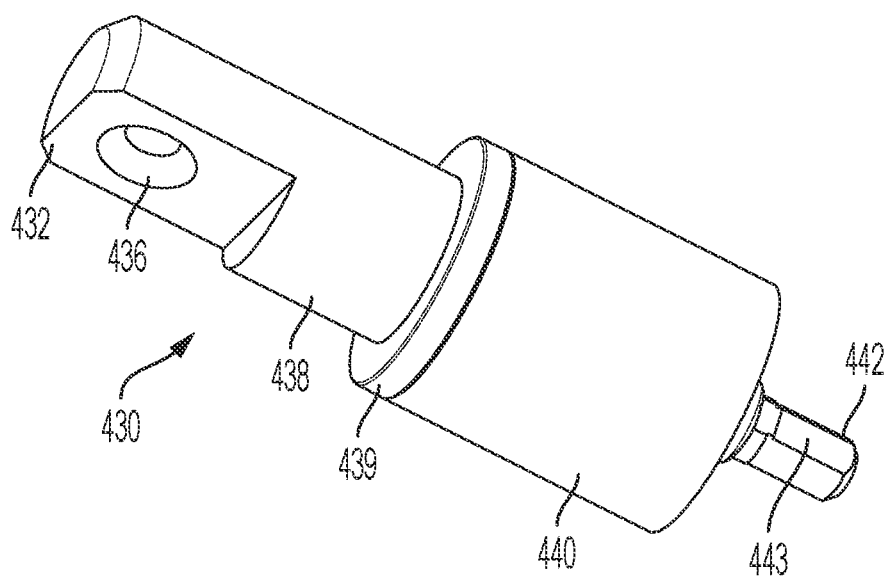
FIGS. 24 and 25 are perspective views of an axle of the pivot assembly of FIGS. 22 and 23.
Figure 25:
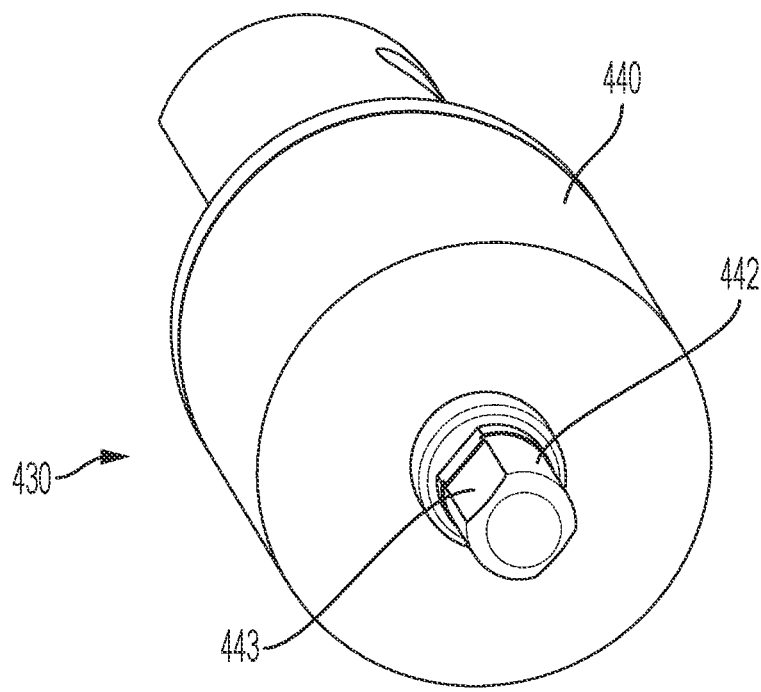
Figure 29:
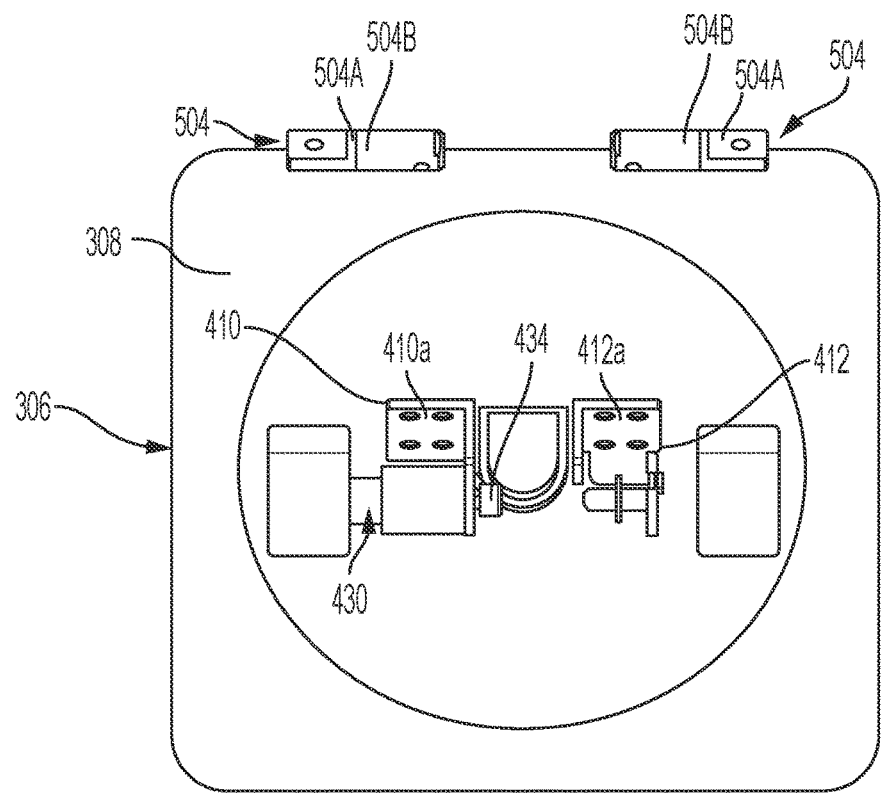
Figure 30:
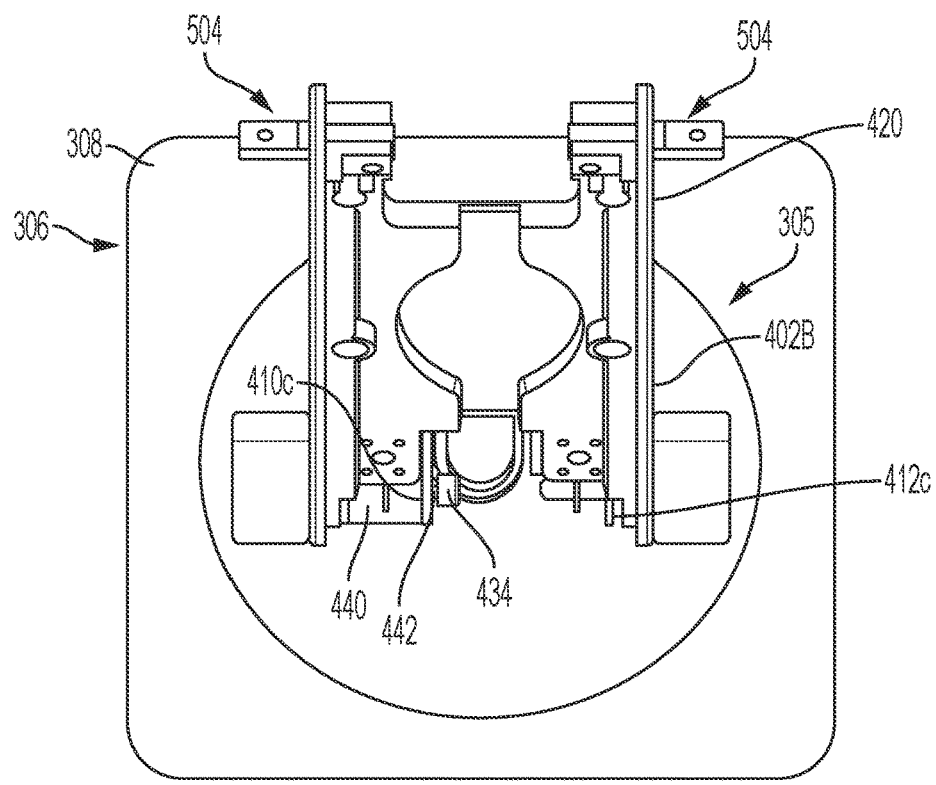

Referring to FIGS. 21 to 23, pivot assembly supports 342 form part of pivot assembly support bushing 340, as described earlier, and include upwardly extending arms and laterally extending tabs, each tab having a hole therethrough. The tabs extend laterally from the tabs, presenting a flat horizontal surface on which second pivot assembly 305 can be mounted. Referring to FIG. 21, arm 400 comprises a housing 402 having a first housing part 400A attached to a second housing part 402B with a body 420 (shown in FIG. 22) therebetween. Second pivot assembly 305 includes body supports 410, 412. Each body support comprises a body mount wall 410a, 412a with holes. Body 420 has matching holes. Fasteners (not shown) pass through the holes and are secured to the body to secure body supports 410, 412 to body 420. A similar arrangement may be provided with first pivot assembly 500. Body support 410 also includes an inner wall 410b, perpendicular to body mount wall 410a, which has a hole 410d configured to receive a portion of a pivot axle 430 (shown in FIGS. 24 and 25) that secures body support 410 to one of pivot assembly supports 342. Inner wall 410b mates with a matching surface of body 420 providing lateral stability. Body support 412 includes an inner wall 412b, which mates with a matching surface of body 420, and an outer wall 412c laterally offset from inner wall 412b and comprising a hole 410d sized to receive a portion of a pivot axle and thus secure body support 412 to the other of pivot assembly supports 342.

Referring now to FIGS. 22 and 23, body support 410 is secured to pivot assembly support 342 by pivot axle 430 and a nut 434. An opposite pivot axle (not shown) secures body support 412 to the other pivot assembly support 342. Pivot axle 430, described with reference to FIGS. 24 and 25, includes a support portion 438 including a flat surface 432 and a hole 436. A fastener, e.g. screw, bolt, pin, rivet or the like, passes through hole 436 while flat surface 432 rests on pivot assembly supports 342 to secure pivot axle 430 and prevent its rotation. A diameter of support portion 438 expands at 439 to match the diameter of a middle portion 440. A nut end 442 extends from middle portion 440 and has a flat section 443. A coil spring (not shown) may be placed inside middle portion 440 to bias the arm or create a lateral force to act as a brake and create enough resistance to permit it to remain in the position chosen by the user. In one example, a coil sleeve is sized and structured to rotate with body support 410 in a known manner causing the coil to expand or tighten and thus operate as a position brake.

Pivot axle 430 can be preassembled to facilitate assembly of support bracket 300. A rubber, polymeric, or other compressible member can be used instead of a coil spring. The flat section matches hole 410d of body support 410, thus causing it to remain at a fixed angle relative to flat section 443.

Referring now to FIGS. 26 to 30 first pivot assembly 500 includes a base 510 secured to display module 20 and a cover 502 over base 510. A pair of pivot axles 504, each including first and second portions 504A and 504B, are mounted onto pivot assembly supports 514 (similar in structure as pivot assembly support 342) of base 510. Pivot axles 504 are described with reference to FIGS. 31 to 33. It should be understood that any other axle can be used, including pivot axle 430. Also shown is a pivot stop or limit surface 540A provided in first portion 504A and operable to cooperate with a corresponding pair of pivot stop or limit surfaces 540B of second portion 504B.

Figure 31:
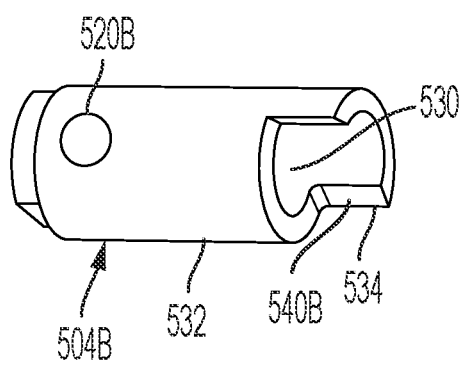
Figure 32:
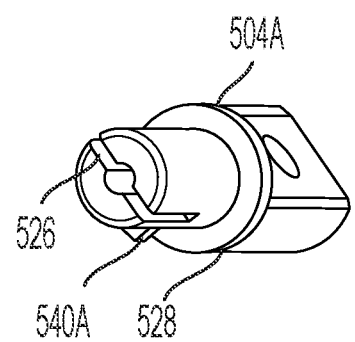
Figure 33:
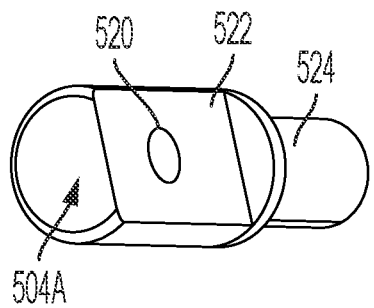

Referring now to FIGS. 31 to 33, first portion 504A has a hole 520 and a flat surface 522 to secure pivot axle 504 to pivot assembly support 514 with a fastener, as discussed with reference to second pivot assembly 305. Securement by the fastener may occur first and then the cover 502 may be added. First portion 504A also has a slotted shaft 524 including a slot 526. Second portion 504B is tubular and has an axial hole 530 sized to receive slotted shaft 524. The diameter of slotted shaft 524 is greater than the diameter of axial hole 530. When the slotted shaft is inserted into the axial hole the slot is compressed and thus provides a radial braking force that can be designed by selecting the appropriate materials and diameters to generate the desired amount of force and friction, as is known in the art. Of course, the arrangement of pivot assembly 305 can also be used in pivot assembly 500. Any assembly capable of maintaining the angular position of the arm and display module may be used instead. First portion 504A also comprises a protrusion providing pivot stop or limit surfaces 540A. The protrusion can extend radially from the external diameter of slotted shaft 524 or longitudinally from the surface 528 from which shaft 524 extends. Second portion 504B comprises a hole 520B through which a fastener (not shown) connects body 420 to prevent rotation therebetween. Second portion 504B also comprises a cylindrical wall 532 and an arcuate or partly-cylindrical wall 534 extending therefrom and including a pair of pivot stop or limit surfaces 540B. Once the slotted shaft is inserted into the axial hole and base 520 rotates, limit surfaces 540A will contact limit surfaces 540B to define the pivot limits of first pivot assembly 500.

Further examples of the embodiments described above include:

Item 1. A video processing system comprising: a video processing apparatus (VPA) including: a housing having a top wall spaced apart from a bottom wall, the top wall having a top wall periphery, a top surface extending to the top wall periphery, and a central area within the top wall periphery; an input port adapted to receive video input signals from a videoscope; an output connector adapted to transmit video output signals corresponding to the video input signals for presentation with a display module; and a bracket interface supported by the housing and adapted to support a support bracket including a first retention feature, the bracket interface located within the central area of the top wall and comprising a bracket base receptacle and a second retention feature, the bracket base receptacle sized and shaped to receive a base end of the support bracket, and the second retention feature sized and shaped to cooperate with the first retention feature to removably retain the base end of the support bracket.

Item 2. The video processing system of item 1, wherein the bracket interface defines a bracket interface periphery in the top surface, and wherein the bracket interface periphery is elevated relative to the top wall periphery.

Item 3. The video processing system of item 2, wherein the top surface curves between the bracket interface periphery to the top wall periphery.

Item 4. The video processing system of item 3, wherein the top surface extends convexly between the bracket interface periphery and the top wall periphery.

Item 5. The video processing system of item 3, wherein the top surface extends in a continuous manner from the bracket interface periphery to the top wall periphery.

Item 6. The video processing system of any of the preceding items, further comprising the support bracket including an arm, wherein the base end includes a swivel assembly operable to rotate the arm about a first axis.

Item 7. The video processing system of item 6, wherein the support bracket comprises the base end opposite a display end, wherein the arm extends between the base end and the display end, wherein the display end includes a first pivot assembly adapted to rotate a display module about a second axis different than the first axis.

Item 8. The video processing system of item 7, wherein the base end includes a second pivot assembly operable to rotate the arm about a third axis parallel to the second axis.

Item 9. The video processing system of item 8, wherein the swivel assembly comprises a swivel frame, a friction plate, and a pivot assembly support, the friction plate positioned between the swivel frame and the pivot assembly support.

Item 10. The video processing system of item 9, wherein the friction plate comprises a textured surface configured to provide a predetermined amount of swivel resistance to the swivel assembly.

Item 11. The video processing system of item 7, wherein the swivel assembly comprises a swivel frame, a friction plate, and a pivot assembly support, the friction plate positioned between the swivel frame and the pivot assembly support.

Item 12. The video processing system of item 11, wherein the friction plate comprises a textured surface configured to provide a predetermined amount of swivel resistance to the swivel assembly.

Item 13. The video processing system of any of the preceding items, further comprising a display module connected to the support bracket by the first pivot assembly.

Item 14. The video processing system of any of the preceding items, further comprising a blank cover removably attachable to the bracket interface.

Item 15. A method of assembly of the video processing system of any of the preceding claims, comprising: providing a video processing apparatus (VPA) including: a housing having a top wall spaced apart from a bottom wall, the top wall having a top wall periphery, a top surface extending to the top wall periphery, and a central area within the top wall periphery; an input port adapted to receive video input signals from a videoscope; an output connector adapted to transmit video output signals corresponding to the video input signals for presentation with a display module; and a bracket interface supported by the housing and adapted to support a support; the method further comprising removably securing the bracket, the bracket including a first retention feature, the bracket interface located within the central area of the top wall and comprising a bracket base receptacle and a second retention feature, the bracket base receptacle sized and shaped to receive a base end of the support bracket, and the second retention feature sized and shaped to cooperate with the first retention feature to removably retain the base end of the support bracket.

Item 16. The method of item 15, further comprising removing the bracket and attaching a blank cover to the bracket interface.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment.

Top, bottom, upward and downward are terms relative to a support structure onto which VPA 100 rests. Thus, the bottom wall is closest to the support structure and the top wall is further away therefrom. Upward indicates from bottom to top, and downward indicates from top to bottom. Lateral refers to elements positioned between the top and bottom walls at a distance from a vertical centerline of housing 110 passing through point C.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The scope of the invention is to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

PART LABELS

| Part Number | Description |
| --- | --- |
| 1 | videoscope |
| 2 | handle |
| 3 | articulation lever |
| 4 | insertion tube |
| 5 | articulation section |
| 6 | image sensor |
| 12 | cable |
| 13 | connector |
| 1a, 1b, 1c | videoscopes |
| 50 | video processing system |
| 22 | cable |
| 29 | display module |
| 30 | support bracket |
| 100 | VPA |
| C | centered on point |
| D1 and D2 | diagonal lines |
| s | surface line |
| h | horizontal line |
| d | distance line |
| 110 | housing |
| 112, 114, 116, 118 | lateral walls |
| 120 | upper periphery |
| 122 | lower periphery |
| 126 | input port |
| 128 | USB port |
| 129 | power button |
| 130 | top wall |
| 132 | bottom wall |
| 134 | standoffs |
| 140 | top surface |
| 150 | bracket interface |
| 152 | bracket interface periphery |
| 154 | bracket base receptacle |
| 156 | walls |
| 157 | second retention feature |
| 158 | recesses |
| 159 | internal space |
| 160 | central area |
| 170 | ventilation grids |
| 172 | heat sink |

-continued

| Part Number | Description |
|---|---|
| 174 | fins |
| 176 | video output port |
| 180 | rear recess |
| 182 | overhang |
| 190 | connector ring |
| 192 | alignment indicator |
| 194 | frame |
| 196 | plug hood |
| 197 | intermediate portion |
| 198 | retention portion |
| 200 | support frame |
| 202, 204, and 206 | opening/cutout |
| 210 | circuit board |
| 212, 214 and 216 | video interface circuits |
| 220 | processor |
| 222 | memory |
| 224 | graphical user interface logic |
| 226 | field-programmable gate array |
| 228 | video output board |
| 229 | video output connector |
| 230 | user interface |
| 240 | through-hole in bottom wall |
| 300 | support bracket |
| 300A | base end |
| 300B | display end |
| 304 | swivel assembly |
| 305 | second pivot assembly |
| 306 | swivel base |
| 306A | blank cover |
| 308A | top wall |
| 308 | top wall |
| 310 | side wall |
| 312 | circular wall |
| 314 | through-hole |
| 316 | first retention feature |
| 317 | tabs |
| 318 | tab protrusions |
| 320 | swivel frame |
| 316 | pivot covers |
| 310 | wall |
| 320 | swivel frame |
| 322 | support plate |
| 324 | circular protrusion |
| 326 | top wall |
| 327 | stop surface |
| 328 | hole |
| 330 | friction plate |
| 332 | textured surface |
| 334 | alignment slots |
| 336 | central aperture |
| 340 | pivot assembly support bushing |
| 342 | pivot assembly supports |
| 344 | central aperture |
| 346 | second pivot assembly supports |
| 350 | swivel axle |
| 351 | collar |
| 352 | shaft |
| 354 | arcuate section |
| 356 | straight section |
| 360 | cable retainer |
| 362 | top surface |
| 364 | circumferential wall |
| 370 | swivel assembly cover |
| 372 | top surface |
| 374 | circular wall |
| 376 | pivot assembly support cover |
| 378 | aperture |
| 380 | position plate |
| 382 | aperture |
| 384 | stop surface |
| 390 | position plate |
| 392 | aperture |
| 394 | stop surface |
| 400 | arm |
| 402 | housing |
| 402A | first housing part |
| 402B | second housing part |
| 410 | body support |
| 410a | body mount wall |
| 410b | inner wall |
| 410d | hole |
| 412 | body supports |
| 412a | body mount wall |
| 412b | inner wall |
| 412c | outer wall |
| 412d | hole |
| 420 | body |
| 430 | pivot axle |
| 432 | flat surface of first section |
| 434 | nut |
| 436 | hole |
| 438 | support portion |
| 439 | collar/expanded diameter |
| 440 | middle portion |
| 442 | nut end |
| 443 | flat surface of nut end |
| 500 | first pivot assembly |
| 502 | base cover |
| 504 | pivot axle |
| 504A | first portion |
| 504B | second portion |
| 510 | display module support base |
| 514 | pivot assembly supports |
| 520 | hole |
| 520B | hole |
| 522 | flat surface |
| 524 | slotted shaft |
| 526 | slot |
| 528 | surface |
| 530 | axial hole |
| 532 | cylindrical wall |
| 534 | wall |
| 540A | pivot stop or limit surface |
| 540B | pivot stop or limit surface |

We claim:

1. A video processing system comprising:
a video processing apparatus (VPA) including:
a housing having a top wall spaced apart from a bottom wall, the top wall having a top wall periphery, a top surface extending to the top wall periphery, and a central area within the top wall periphery;
an input port adapted to receive video input signals from a videoscope;
an output connector adapted to transmit video output signals corresponding to the video input signals for presentation with a display module;
a support bracket including a base end, an arm and a first retention feature; and
a bracket interface supported by the housing and adapted to support the support bracket, the bracket interface located within the central area of the top wall and comprising a bracket base receptacle and a second retention feature, the bracket base receptacle sized and shaped to receive the base end of the support bracket, and the second retention feature sized and shaped to cooperate with the first retention feature to removably retain the base end of the support bracket,
wherein the base end includes a swivel assembly operable to rotate the arm about a first axis,
wherein the bracket interface defines a bracket interface periphery in the top surface, and
wherein the bracket interface periphery is elevated relative to the top wall periphery.

2. The video processing system of claim 1, wherein the top surface curves between the bracket interface periphery to the top wall periphery.

3. The video processing system of claim 2, wherein the top surface extends convexly between the bracket interface periphery and the top wall periphery.

4. The video processing system of claim 2, wherein the top surface extends in a continuous manner from the bracket interface periphery to the top wall periphery.

5. The video processing system of claim 1, wherein the support bracket comprises a display end opposite the base end, wherein the arm extends between the base end and the display end, wherein the display end includes a first pivot assembly adapted to rotate the display module about a second axis different than the first axis, and wherein the base end includes a second pivot assembly operable to rotate the arm about a third axis parallel to the second axis.

6. The video processing system of claim 5, wherein the swivel assembly comprises a swivel frame, a friction plate, and a pivot assembly support, the friction plate positioned between the swivel frame and the pivot assembly support.

7. The video processing system of claim 6, wherein the friction plate comprises a textured surface configured to provide a predetermined amount of swivel resistance to the swivel assembly.

8. The video processing system of claim 1, wherein the swivel assembly comprises a friction plate, and wherein the friction plate comprises a textured surface configured to provide a predetermined amount of swivel resistance to the swivel assembly.

9. The video processing system of claim 1, further comprising a first pivot assembly and the display module, the display module connected to the support bracket by the first pivot assembly.

10. The video processing system of claim 9, further comprising the videoscope, the videoscope having an insertion tube with an articulation section and an image sensor disposed at a distal end of the articulation section.

11. The video processing system of claim 1, further comprising a blank cover removably attachable to the bracket interface.

12. The video processing system of claim 1, further comprising the videoscope and the display module.

13. The video processing system of claim 1, wherein the support bracket comprises a display end opposite the base end, wherein the arm extends between the base end and the display end, wherein the display end includes a first pivot assembly adapted to rotate the display module about a second axis different than the first axis.

14. The video processing system of claim 1, wherein the swivel assembly comprises a swivel frame, a friction plate, and a pivot assembly support, the friction plate positioned between the swivel frame and the pivot assembly support.

15. A video processing system comprising: a video processing
apparatus (VPA) including:
a housing having a top wall spaced apart from a bottom wall, the top wall having a top wall periphery, a top surface extending to the top wall periphery, and a central area within the top wall periphery;
an input port adapted to receive video input signals from a videoscope;
an output connector adapted to transmit video output signals corresponding to the video input signals for presentation with a display module;
a support bracket including a base end, an arm and a first retention feature; and
a bracket interface supported by the housing and adapted to support the support bracket, the bracket interface located within the central area of the top wall and comprising a bracket base receptacle and a second retention feature, the bracket base receptacle sized and shaped to receive the base end of the support bracket, and the second retention feature sized and shaped to cooperate with the first retention feature to removably retain the base end of the support bracket,
wherein the base end includes a swivel assembly operable to rotate the arm about a first axis,
wherein the support bracket comprises a display end opposite the base end, wherein the arm extends between the base end and the display end, wherein the display end includes a first pivot assembly adapted to rotate the display module about a second axis different than the first axis,
wherein the base end includes a second pivot assembly operable to rotate the arm about a third axis parallel to the second axis,
wherein the swivel assembly comprises a swivel frame, a friction plate, and a pivot assembly support, the friction plate positioned between the swivel frame and the pivot assembly support, and
wherein the friction plate comprises a textured surface configured to provide a predetermined amount of swivel resistance to the swivel assembly.

16. The video processing system of claim 15, wherein the bracket interface defines a bracket interface periphery in the top surface, and wherein the bracket interface periphery is elevated relative to the top wall periphery.

17. The video processing system of claim 15, further comprising the videoscope and the display module.

18. A video processing
system comprising: a video processing apparatus (VPA) including:
a housing having a top wall spaced apart from a bottom wall, the top wall having a top wall periphery, a top surface extending to the top wall periphery, and a central area within the top wall periphery;
an input port adapted to receive video input signals from a videoscope;
an output connector adapted to transmit video output signals corresponding to the video input signals for presentation with a display module;
a support bracket including a base end, an arm and a first retention feature; and
a bracket interface supported by the housing and adapted to support the support bracket, the bracket interface located within the central area of the top wall and comprising a bracket base receptacle and a second retention feature, the bracket base receptacle sized and shaped to receive the base end of the support bracket, and the second retention feature sized and shaped to cooperate with the first retention feature to removably retain the base end of the support bracket,
wherein the base end includes a swivel assembly operable to rotate the arm about a first axis, and
wherein the swivel assembly comprises a swivel frame, a friction plate, and a pivot assembly support, the friction plate positioned between the swivel frame and the pivot assembly support, and
wherein the friction plate comprises a textured surface configured to provide a predetermined amount of swivel resistance to the swivel assembly.

19. The video processing system of claim 18, wherein the bracket interface defines a bracket interface periphery in the top surface, and wherein the bracket interface periphery is elevated relative to the top wall periphery.

20. The video processing system of claim 18, further comprising the videoscope and the display module.

\* \* \* \* \*